(12) United States Patent
Abhijitsinh et al.

(10) Patent No.: US 9,381,303 B2
(45) Date of Patent: Jul. 5, 2016

(54) STERILITY BARRIER FOR PEN NEEDLE AND STORAGE CONTAINER THEREFOR

(75) Inventors: Raj Abhijitsinh, Parsippany, NJ (US); Sean Sullivan, Ridgewood, NJ (US); Robert Banik, Long Valley, NJ (US); James S. Bates, Sparta, NJ (US); Cole Constantineau, Cambridge, MA (US); Ryan Schoonmaker, San Marcos, CA (US); Michel Bruehwiler, Newton, MA (US); Joshua D. Horvath, Sparta, NJ (US); Doug Lawrence, Kinnelon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1141 days.

(21) Appl. No.: 13/205,466

(22) Filed: Aug. 8, 2011

(65) Prior Publication Data

US 2012/0041381 A1    Feb. 16, 2012

Related U.S. Application Data

(60) Provisional application No. 61/344,534, filed on Aug. 16, 2010.

(51) Int. Cl.
*A61M 5/32* (2006.01)
*A61M 5/24* (2006.01)
*A61M 5/00* (2006.01)
(Continued)

(52) U.S. Cl.
CPC .............. *A61M 5/2455* (2013.01); *A61M 5/002* (2013.01); *A61M 5/008* (2013.01); *A61M 2005/312* (2013.01); *A61M 2005/3117* (2013.01);
(Continued)

(58) Field of Classification Search
CPC . A61M 5/003; A61M 5/3202; A61M 5/3205; A61M 2005/3117; A61M 2005/312; A61M 5/002; A61M 5/008; A61M 5/2455
USPC .......................... 604/192, 272; 206/364–366
See application file for complete search history.

(56) References Cited

U.S. PATENT DOCUMENTS 2,573,311 A    10/1951    Cupler, II
2,771,182 A    11/1956    Messmer
(Continued)

FOREIGN PATENT DOCUMENTS

EP    1421961    5/2004
FR    2623403    5/1989
(Continued)

OTHER PUBLICATIONS

EPO Search Report dated Nov. 25, 2011 issued in Application No. 11177464.2-2320.

*Primary Examiner* — Rebecca E Eisenberg
(74) *Attorney, Agent, or Firm* — Dickinson Wright PLLC

(57) ABSTRACT

A pen needle includes a hub having a first opening at a first end and a second opening at a second end. A needle is connected to the hub and extends through the first opening at the first end. Access to the needle through the second opening is prevented by a sterility barrier, which has a movable portion that is moved along a longitudinal axis of the needle to provide access to the needle. A storage container includes a housing having a plurality of cavities to receive a plurality of pen needles. A cover is rotatably connected to the housing and is rotated such that an access portion thereof is aligned with one of the cavities, thereby providing access to the pen needle in the cavity.

20 Claims, 26 Drawing Sheets

(51) Int. Cl.
  *A61M 5/31* (2006.01)
  *A61M 39/26* (2006.01)

(52) U.S. Cl.
  CPC .. *A61M2005/3118* (2013.01); *A61M 2039/267* (2013.01); *Y10T 29/49826* (2015.01)

(56) References Cited

U.S. PATENT DOCUMENTS

| | | | |
|---|---|---|---|
| 4,203,518 A | 5/1980 | Current | |
| 4,383,615 A | 5/1983 | Aquino | |
| 4,449,630 A | 5/1984 | Filhol | |
| 4,524,891 A | 6/1985 | Silva | |
| 4,586,614 A | 5/1986 | Ger | |
| 5,150,788 A | 9/1992 | Weissman | |
| 5,347,078 A | 9/1994 | Eckels | |
| 5,451,213 A | 9/1995 | Teicher | |
| 5,545,145 A | 8/1996 | Clinton | |
| 5,595,296 A | 1/1997 | Wood | |
| 5,799,788 A | 9/1998 | Webb | |
| 5,873,462 A | 2/1999 | Nguyen | |
| 5,971,966 A | 10/1999 | Lav | |
| 5,975,295 A | 11/1999 | Diamond | |
| 6,346,094 B2 * | 2/2002 | West et al. | 604/241 |
| 6,880,701 B2 | 4/2005 | Bergeron | |
| 6,889,830 B2 | 5/2005 | Bergeron | |
| 6,923,319 B1 | 8/2005 | Erickson | |
| 7,134,550 B2 | 11/2006 | Groth | |
| 7,207,976 B2 | 4/2007 | Hansen | |
| 2003/0015444 A1 | 1/2003 | Molin | |
| 2007/0299394 A1 | 12/2007 | Rolfe | |
| 2009/0014462 A1 | 1/2009 | Costa | |
| 2009/0069752 A1 * | 3/2009 | Raj et al. | 604/192 |
| 2012/0029440 A1 | 2/2012 | Boyd | |
| 2013/0105345 A1 * | 5/2013 | Van der Beek et al. | 206/366 |

FOREIGN PATENT DOCUMENTS

| | | |
|---|---|---|
| JP | H11146912 A | 6/1999 |
| JP | 2004505683 | 2/2004 |
| JP | 2010534542 A | 11/2010 |
| WO | 9936108 | 7/1999 |
| WO | 0193927 | 12/2001 |
| WO | 0211797 | 2/2002 |
| WO | 02100465 | 12/2002 |
| WO | 2009016161 A1 | 2/2009 |

* cited by examiner

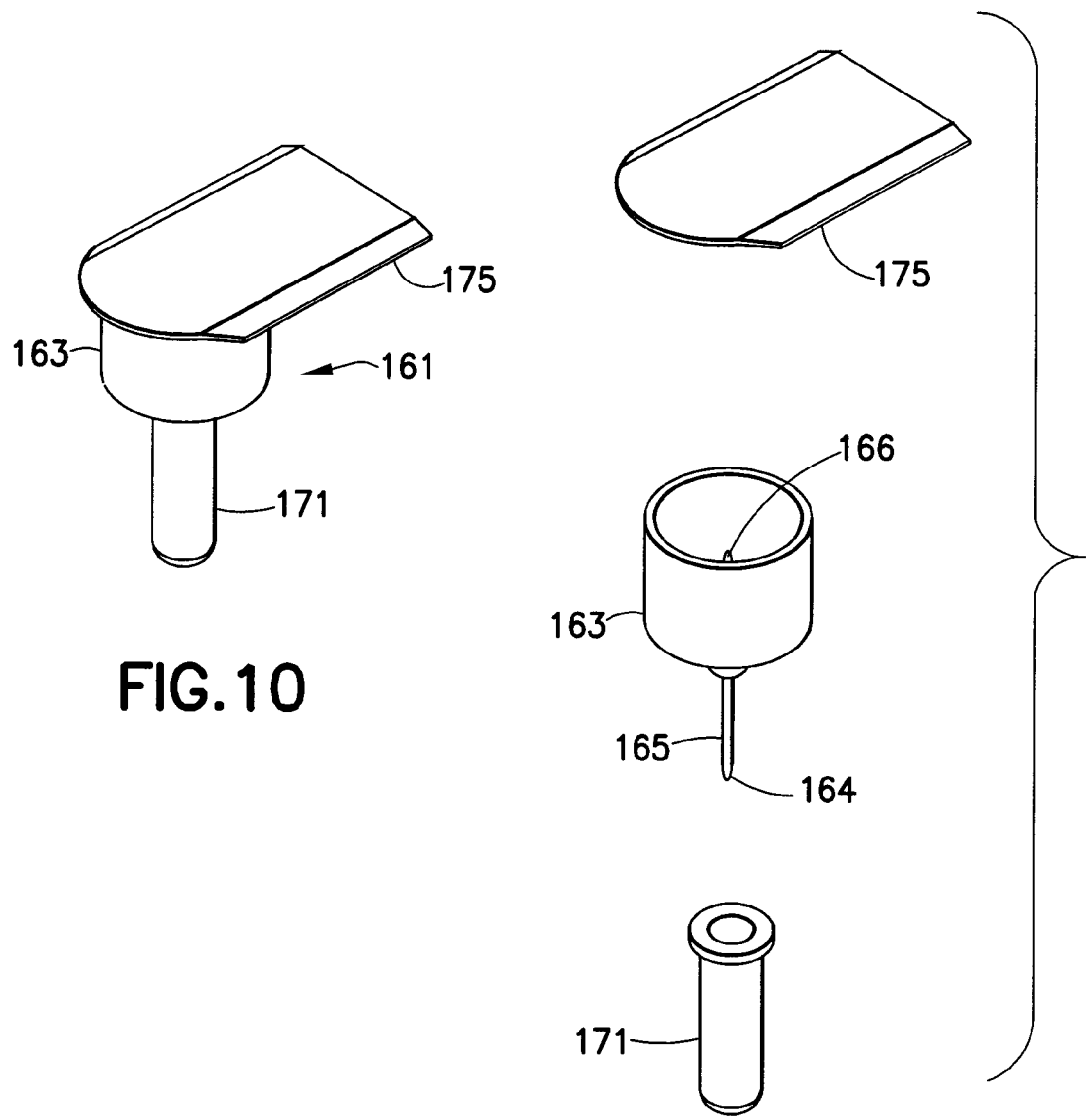

STERILITY BARRIER FOR PEN NEEDLE AND STORAGE CONTAINER THEREFOR

CROSS REFERENCE TO RELATED APPLICATION

This application claims the benefit under 35 U.S.C. §119 (e) of U.S. Provisional Application Ser. No. 61/344,534, filed Aug. 16, 2010, which is hereby incorporated by reference in its entirety.

FIELD OF THE INVENTION

The present invention relates to a sterility barrier for a pen needle for use with an injection apparatus. The present invention also relates to a storage container for pen needles having sterility barriers. More particularly, the present invention relates to a sterility barrier that is not removed from the pen needle for use. Still more particularly, the present invention relates to a storage container that provides access to the sterility barrier of a pen needle with an injection apparatus.

BACKGROUND OF THE INVENTION

In certain circumstances, it is desirable to inject medication directly into human tissue. Typically, syringes or pen injection devices are used to inject medicaments into tissue areas, such as the intramuscular tissue layer, the subcutaneous tissue layer, and the intradermal tissue layer.

The assembly and operation of a typical pen injection device is described in commonly-assigned U.S. Pat. No. 7,645,264, which is hereby incorporated by reference in its entirety.

Pen injection devices, such as an exemplary pen injector 100, as shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 100 in a shirt pocket, purse, or other suitable location.

FIG. 2 is an exploded view of the exemplary drug delivery pen shown in FIG. 1. The dose knob/button 24 has a dual purpose and is used to both set the dosage of the medication to be injected and to inject the dosed medicament via the lead screw 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail herein as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used such as attaching to the cartridge. To protect a user, or anyone who handles the drug delivery pen 100, an outer cover 69, which attaches to the hub 20, covers the hub. An inner shield 59 covers the patient needle 11 within the outer cover 69. The inner shield 59 can be secured to the hub 20 to cover the patient needle 11 by any suitable means, such as an interference fit or a snap fit. The outer cover 69 and inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

A pen needle, which includes the hub 20, needle 11, outer shield 69 and inner shield 59, is typically used for a single injection and is then disposed of. Typically, pen needles are packaged individually and disposed loose in a container, such as a box or carton. Each pen needle is sealed with a label laminated thereto to provide a sterility barrier. However, such container does not include means for containing used pen needles. Accordingly, a need exists for a storage assembly that stores both new and used pen needles.

Additionally, existing pen needle containers store a large number of new pen needles, which causes the containers to be large and bulky. Hence, the containers are unwieldy and not conducive to being carried. Accordingly, a need exists for a pen needle storage container that can be easily and conveniently carried by a user.

SUMMARY OF THE INVENTION

In accordance with an aspect of the present invention, a storage container stores new pen needles having sterility barriers for use by an injection device.

In accordance with another aspect of the present invention, the storage container stores used pen needles.

In accordance with another aspect of the present invention, the storage container is conducive to being carried by a user.

A storage assembly according to an exemplary embodiment of the present invention includes an upper housing movably connected to a lower housing. A plurality of pen needles having sterility barriers are stored in the lower housing. An opening in the upper housing provides access for withdrawing a new pen needle and disposing of a used pen needle. An injection device moves a portion of the sterility barrier such that a fluid path is created between a medicament cartridge of the injection device and a needle of the pen needle. The upper housing can then be moved to a new position to provide access to another new pen needle.

A pen needle in accordance with exemplary embodiments of the present invention includes a sterility barrier that seals a non-patient end of a pen needle hub. The hub has a first opening at a first end and a second opening at a second end. A needle is connected to the hub and extends through the first opening at the first end. The sterility barrier seals the second opening. The sterility barrier has a movable portion that moves along a longitudinal axis of the needle to provide access to the needle.

A storage container in accordance with exemplary embodiments of the present invention stores new and used pen needles. Each pen needle has a hub with first and second openings. A needle is connected to the hub and passes through the first opening. A housing has a plurality of cavities to receive the plurality of pen needles. A cover is rotatably connected to the housing. The cover is rotated such that an access portion in the cover is aligned with one of the cavities to provide access to the pen needle in the cavity. A sterility barrier prevents access to the needle. A portion of the sterility barrier is movable to access the needle.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which:

FIG. 10 is a perspective view of a new pen needle for storing in the disc storage assembly;

FIG. 11 is an exploded perspective view of the pen needle of FIG. 10;

Throughout the drawings, like reference numbers will be understood to refer to like parts, components and structures.

DETAILED DESCRIPTION OF THE EXEMPLARY EMBODIMENTS

Figure 3:
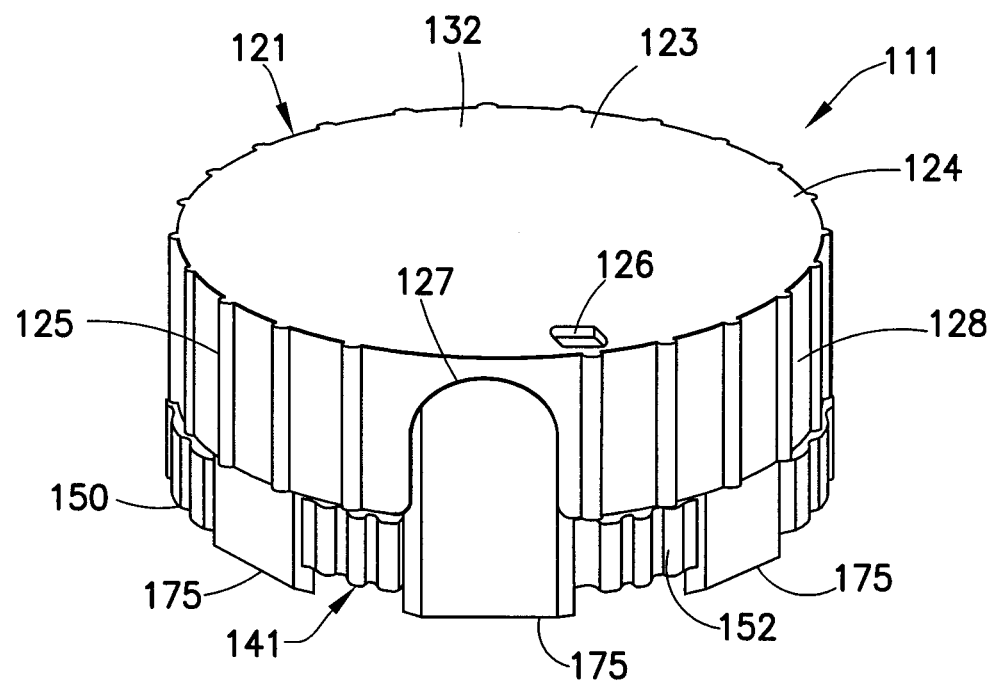
FIG. 3 is a perspective view of a pen needle disc storage assembly according to an exemplary embodiment of the present invention.
Figure 4:
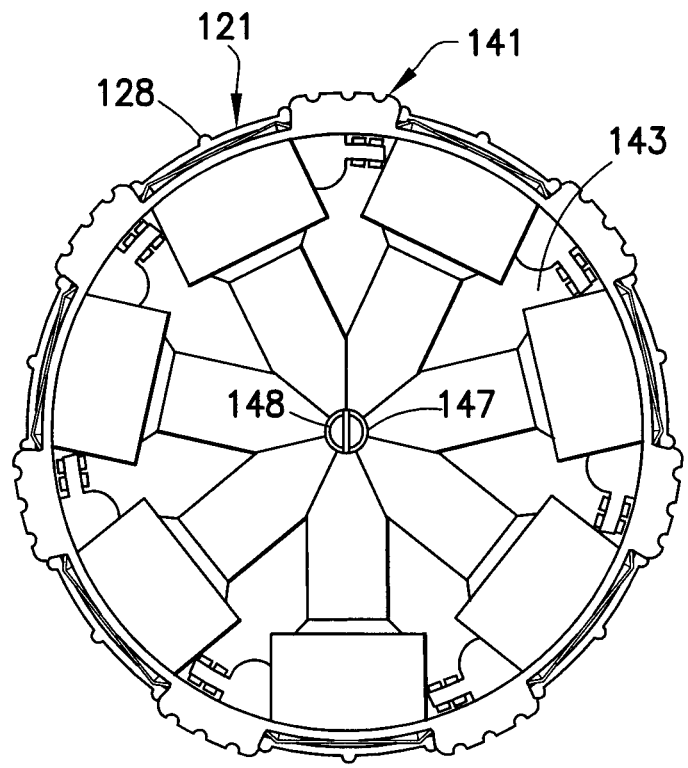
FIG. 4 is a bottom plan view of the disc storage assembly of FIG. 3.

In an exemplary embodiment of the present invention, as shown in FIGS. 3-11, a storage assembly 111 includes an upper housing 121 movably connected to a lower housing 141. A plurality of pen needles 161, as shown in FIGS. 10 and 11, are stored in the storage assembly 111. Preferably, the storage assembly 111 is substantially disc-shaped, although any suitable configuration can be used. A disc-shaped storage assembly 111, as shown in FIG. 3, reduces the overall size of the storage assembly, thereby providing an assembly that is easily and conveniently carried as well as storing both new (sterile) and used pen needles for use with an injection apparatus.

Figure 6:
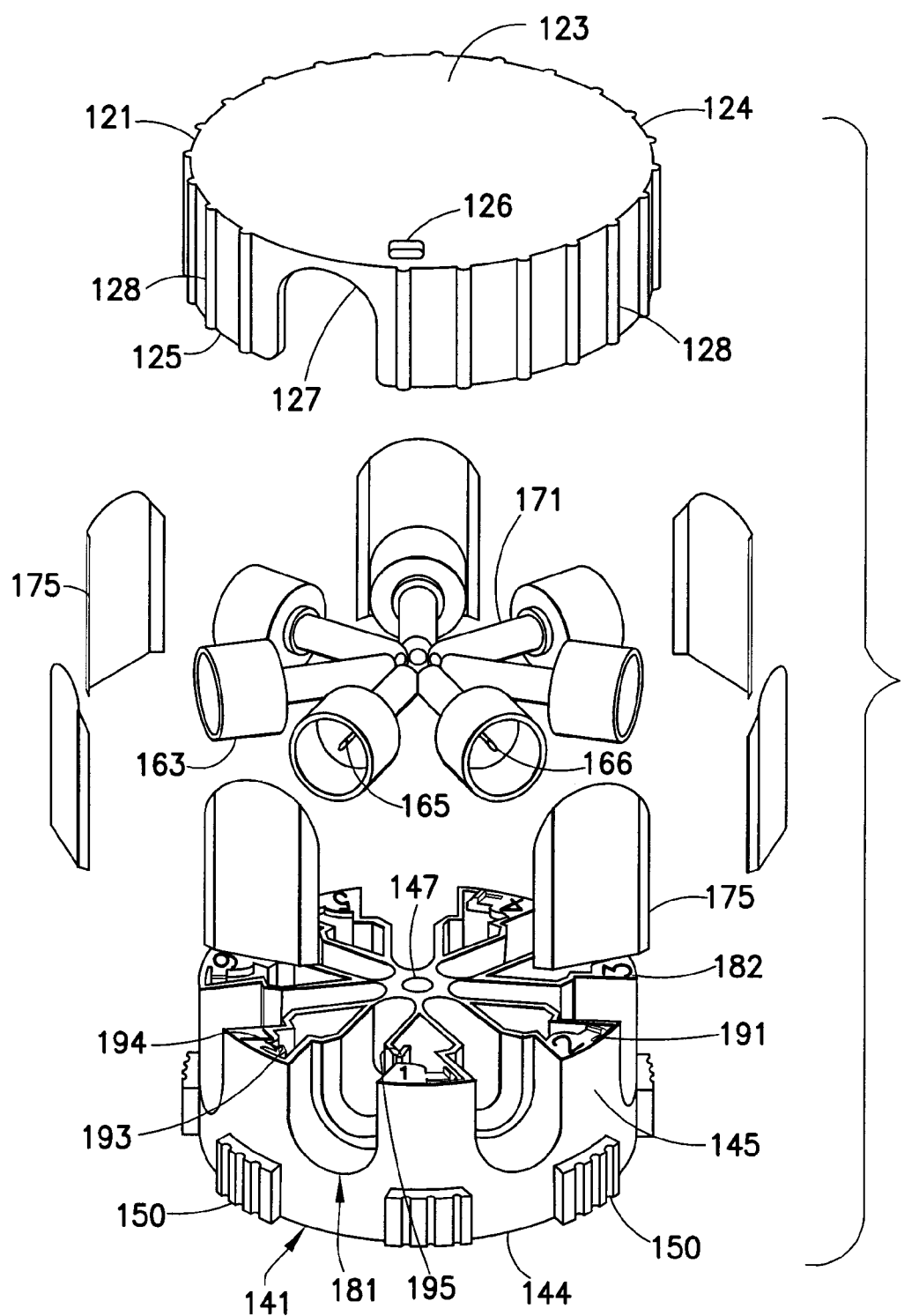
FIG. 6 is an exploded perspective view of the disc storage assembly of FIG. 3.

The upper housing 121 has a substantially planar base 123 with a wall 125 extending downwardly from an outer perimeter 124 of the base 123, as shown in FIGS. 3 and 6. Preferably, the base 123 of the upper housing 121 is substantially circular. An opening 126 is formed in the base 123 such that a user can see through the base. A recess 127 is formed in the wall 125. Ribs 128 extend along the wall 125 to facilitate gripping the wall by a user.

Figure 8:
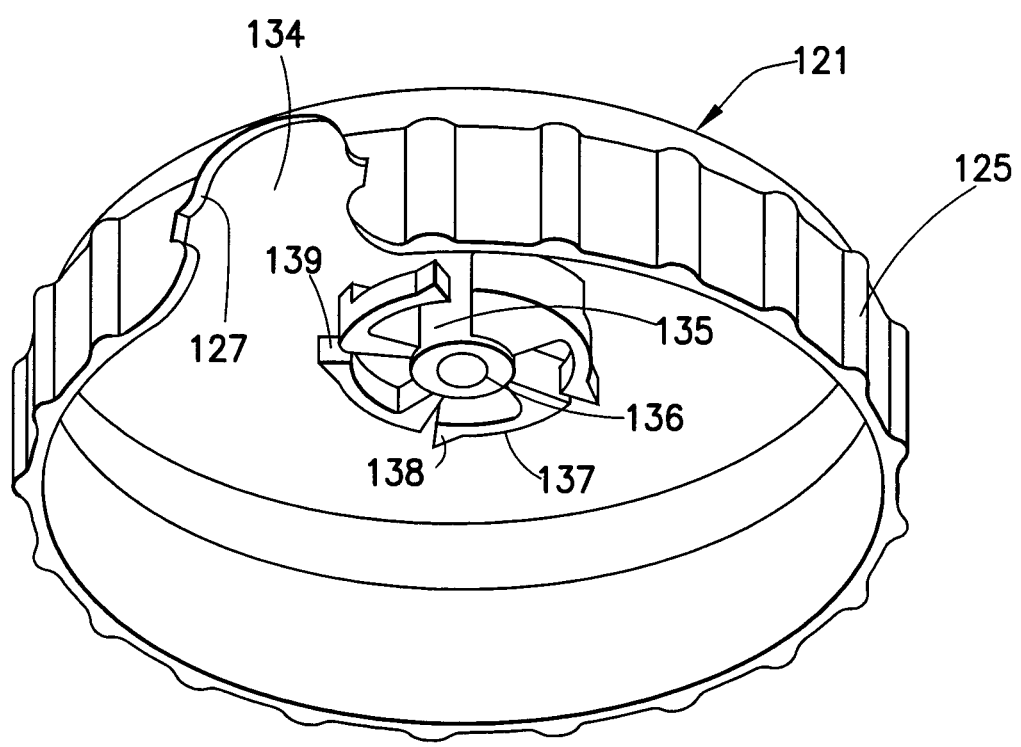
FIG. 8 is a perspective view of the lower surface of the upper housing of FIG. 3.
Figure 9:
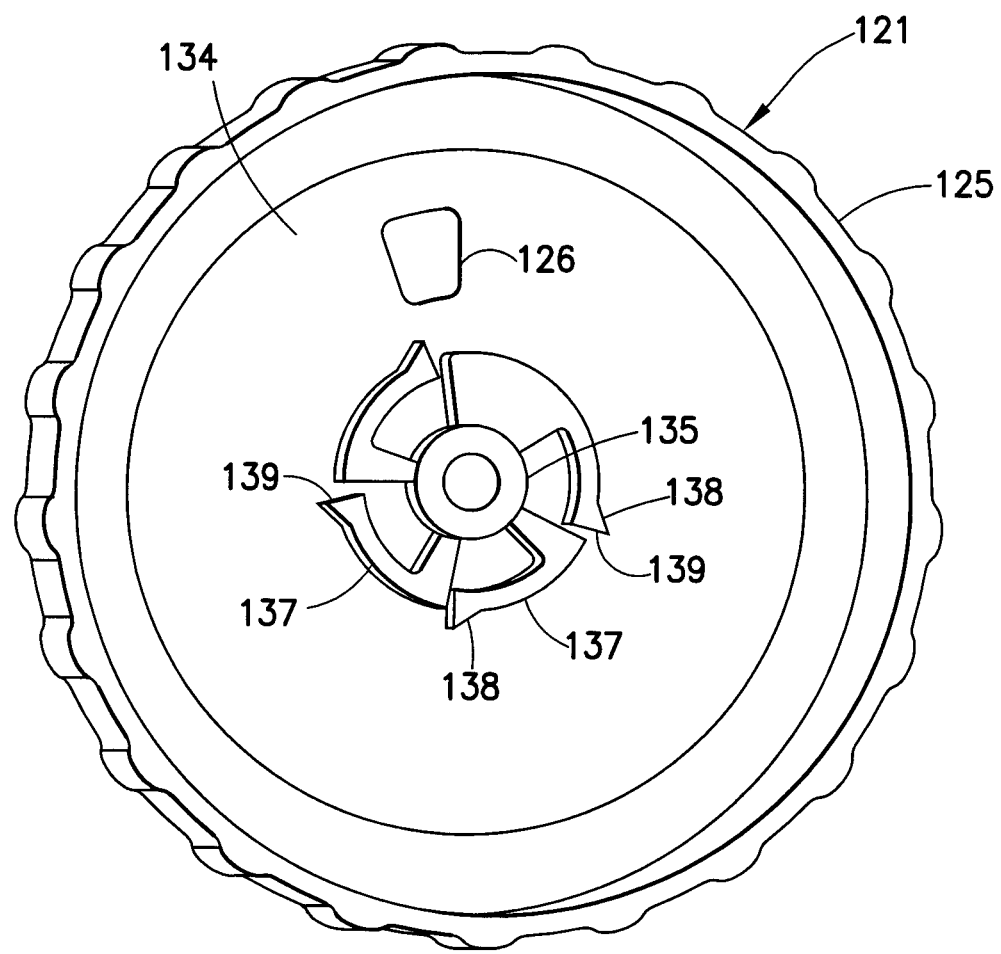
FIG. 9 is a perspective view of the lower surface of the upper housing of FIG. 3 showing the window.

The base 123 of the upper housing 121 has an upper surface 132 and a lower surface 134, as shown in FIGS. 3, 8 and 9. A post 135 extends downwardly from the lower surface 134 of the base 123 of the upper housing 121. An opening 136 formed in the post 135 receives a fastener 148 to secure the upper housing 121 to the lower housing 141. A plurality of flexible arms 137 extend outwardly from the post 135. Ramped surfaces 138 are disposed adjacent free ends 139 of the flexible arms 137.

The lower housing 141 has a base 143 with a wall 145 extending upwardly from an outer perimeter 144 of the base 143. Preferably, the base 143 of the lower housing is substantially circular. A bore 147 passes through the lower housing 141 from the base 143 to an upper surface 149 and is adapted to receive the fastener 148 that is received by a corresponding opening 136 in the post 135 in the upper housing 121, thereby allowing the upper housing 121 to move with respect to the lower housing 141. A plurality of protrusions 150 are connected to the wall 145 of the lower housing to facilitate handling the lower housing by a user. Preferably, a plurality of grooves 152 are disposed in the protrusions 150 to facilitate gripping the protrusions.

Figure 2:
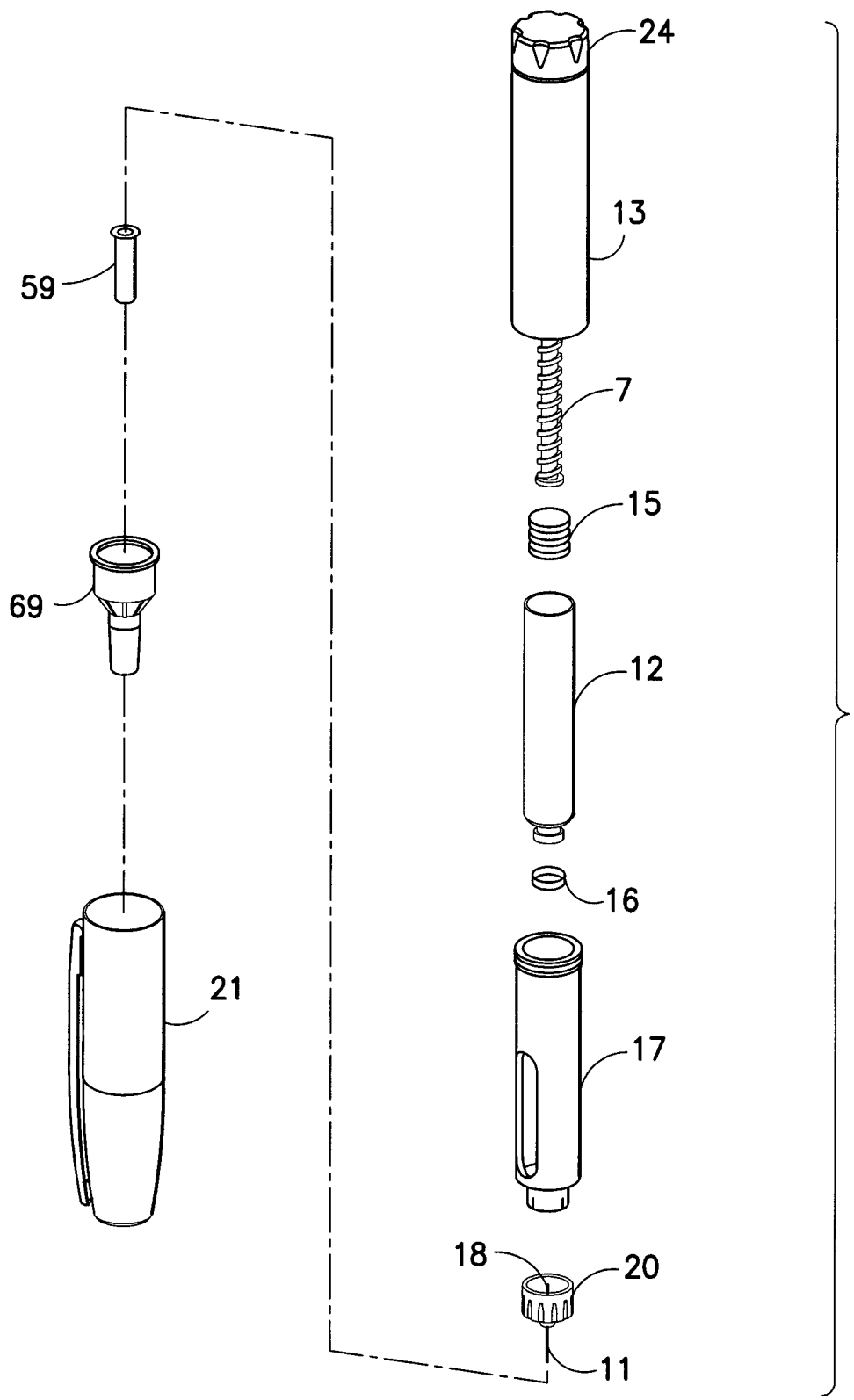
FIG. 2 is an exploded perspective view of the components of the drug delivery pen of FIG. 1.

The pen needle 161, as shown in FIGS. 6, 10 and 11, includes a hub 163 with a needle 165 rigidly connected thereto. The needle has a proximal end 164 for puncturing a user's skin at an injection site and a distal end 166 for piercing a septum 16 of a cartridge 12 of a drug delivery pen 100 (FIG. 2). The pen needle can include a shield 171 disposed over the needle 165, as shown in FIG. 11, to cover the proximal end 164 of the needle, thereby preventing accidental needle sticks. A label 175 is adhered to the hub 163 to provide a sterility barrier at the distal or non-patient end of the needle 165. The pen needle 161 can include an outer cover 69 (FIG. 2). Alternatively, the label 175 can be adhered to the outer cover 69. Alternative sterility barriers are described in the following paragraphs.

The shield 171 covering the proximal or patient end of the needle 165 can be removably connected to the lower housing or integrated into the lower housing 141. The removably connected shield 171 is manually removed by the user after withdrawing the pen needle 161 from the disc storage assembly 111. When the shield is integrated into the lower housing 141, the user does not need to remove the shield from the pen needle after connecting the drug delivery pen to the pen needle and removing the pen needle from the disc storage assembly.

Figure 7:
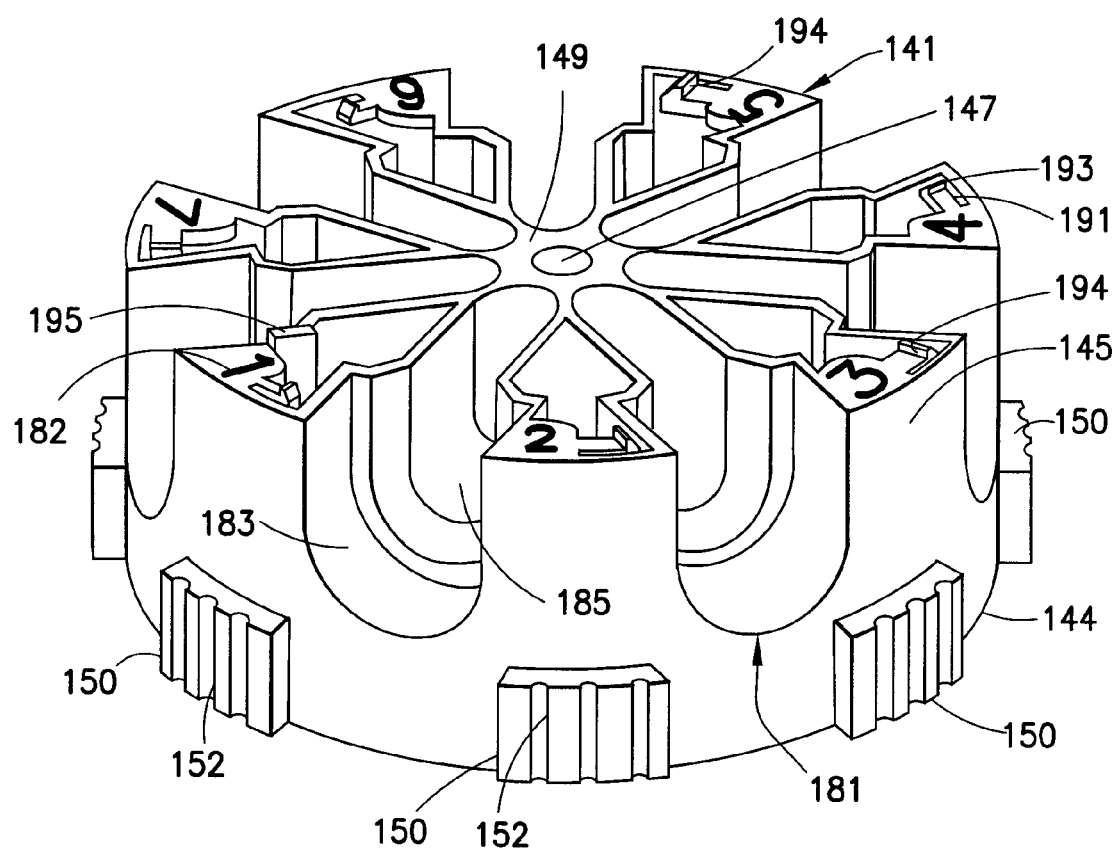
FIG. 7 is a perspective view of a lower housing of the disc storage assembly of FIG. 3.

A plurality of cavities 181 are formed in the lower housing 141. As shown in FIGS. 6 and 7, the lower housing 141 has seven cavities 181. However, the lower housing 141 may have any number of cavities 181. Each cavity 181 receives a pen needle 161 and has a first portion 183 and a second portion 185. The first portion 183 is wider than the second portion 185. The first portion 183 of the cavity 181 receives the hub 163 of the pen needle 161, and the second portion 185 of the cavity 181 receives the patient-end of the needle 165 and the shield 171 of the pen needle 161. A cavity number 182 is indicated on the upper surface 149 of the lower housing 141 adjacent each cavity 181. A plurality of flexible arms 191 are connected to the upper surface 149 of the lower housing 141. A flat surface 194 adjacent the ramped surface 193 of the flexible arm 191 engages a free end 139 of the corresponding flexible arm 137 of the upper housing 121 to prevent the upper housing from being rotated in the counter-clockwise direction as shown in FIGS. 6 and 7. Clockwise rotation rotates the recess 127 in the upper housing 121 to a position providing access to a used pen needle. Ramped surfaces 138 of the flexible arms 137 of the upper housing 121 engage the ramped surfaces 193 of the flexible arms 191 of the lower housing 141, thereby causing the flexible arms 191 of the lower housing 141 to flex downwardly such that the upper housing 121 can be rotated to the next cavity 181.

Figure 5:
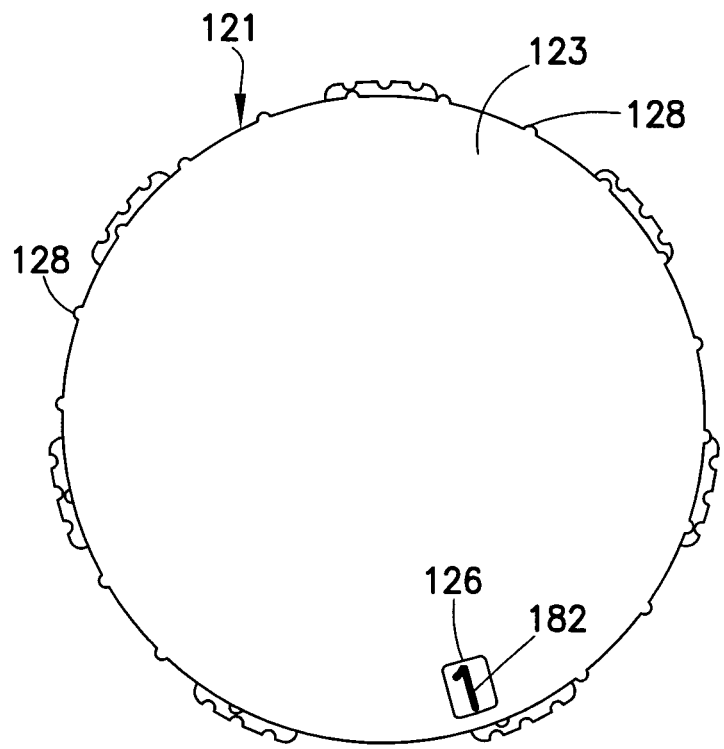
FIG. 5 is a top plan view of the disc storage assembly of FIG. 4.

An assembled disc storage assembly 111 is shown in FIG. 3. The upper housing 121 is rotated with respect to the lower housing 141 such that the recess 127 in the upper housing 121 is aligned with a cavity 181 in the lower housing. A cavity indicator 182 is visible through the opening 126 in the upper housing 121 and indicates the number of new pen needles remaining in the storage assembly 111. For example, as shown in FIG. 5, the number "1" is visible through the opening 126, thereby indicating that the storage assembly is in a position providing access to the last new pen needle. Alternatively, the number visible through the opening can indicate which needle is being used, instead of how many needles are remaining. The ribs 128 of the upper housing 121 and the protrusions 150 of the lower housing 141 facilitate gripping and operating the disc storage assembly 111. The user removes the label tab 175 from the non-patient end of the hub 163, thereby providing access to the cavity and the new (sterile) pen needle 161 stored therein. The drug delivery pen (100, FIG. 1) is inserted into the hub 163, thereby securing the pen needle 161 to the drug delivery pen. The drug delivery pen can be rotated into the hub when a threaded connection is used or pushed into the hub when a snap fit connection is present, although any suitable means of connecting the drug delivery pen and the pen needle may be used.

Figure 43:
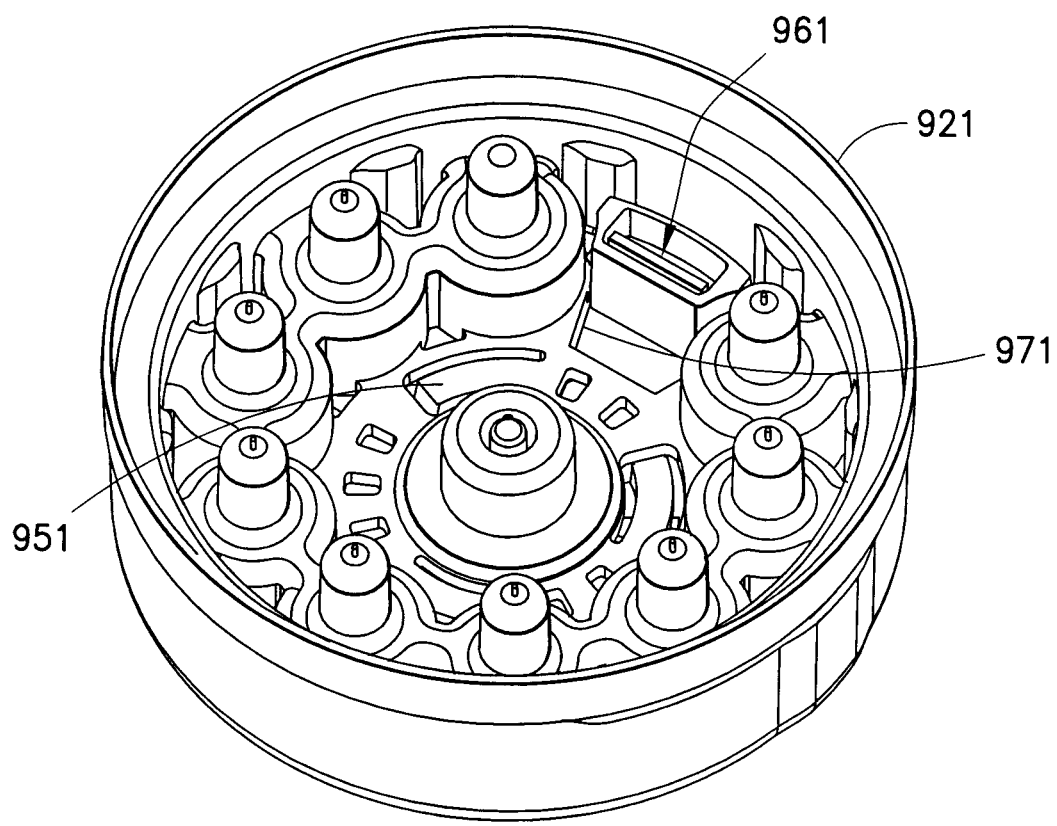
FIG. 43 is a lower perspective view of the storage assembly of FIG. 41 in a locked position.
Figure 45:
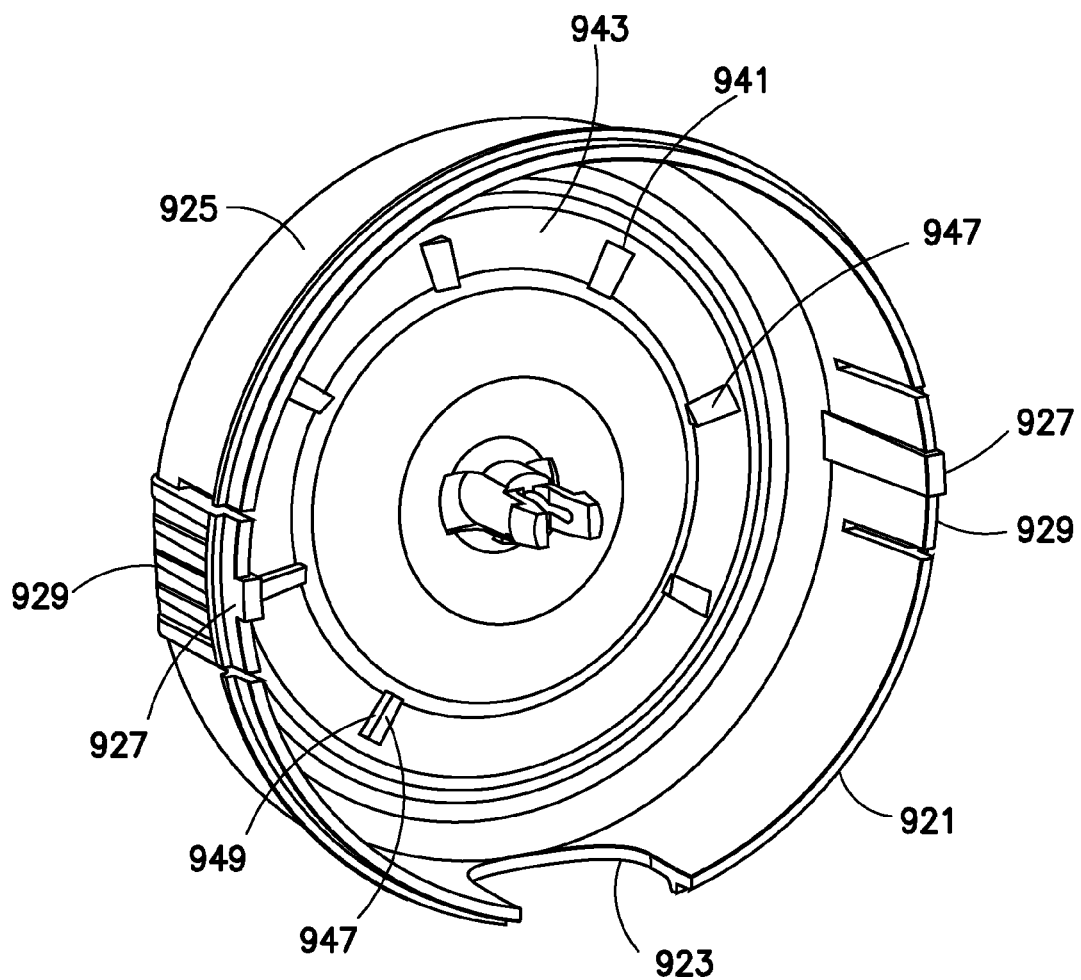
FIG. 45 is a perspective view of an upper housing of a storage assembly in accordance with another exemplary embodiment of the present invention.

Following the injection, the pen needle can be returned to the cavity from which it was withdrawn. Rotating the upper housing 121 to the next cavity (clockwise in FIGS. 3 and 6) causes the wall 125 of the upper housing to cover the access to the cavity containing the used pen needle, thereby shielding the pen needle. The free end 139 of the flex arms 137 of the upper housing 121 engage the flat surfaces 194 of the flex arms 191 of the lower housing 141 to prevent rotating the upper housing 121 in the wrong direction, i.e, counter-clockwise as shown in FIGS. 3 and 6, thereby preventing access to used pen needles. As shown in FIGS. 43 and 45, tabs 941 of the upper housing 921 engage fingers 951 of the lower housing 911 to prevent rotation of the upper housing in the wrong direction. Once the upper housing 121 has been rotated through all the cavities (all the pen needles have been used), a stop member (not shown) of the upper housing 121 engages a stop member 195 extending upwardly from the lower housing 141. The stop member 195 engages the upper housing 121 to prevent further rotation thereof in the clockwise direction. The flat surface 194 of the flexible arm 191 prevents counter-clockwise rotation of the upper housing 121. The entire disc storage assembly 111 can then be disposed of in a manner appropriate for disposing of used needles.

As shown in FIGS. 3-12, a disc storage assembly dispenses new pen needles and contains used pen needles. The pen needles are radially disposed within the substantially disc-shaped storage assembly. Sterility barriers are formed at both the patient and non-patient ends of the needles, and can be formed in any suitable manner. The sterility barrier can be connected to the hub 163 or to the outer cover 69 (FIG. 2) or in any other suitable manner. The sterility barrier creates a seal that prevents microbial interaction. Several exemplary embodiments are discussed below.

Figure 25:
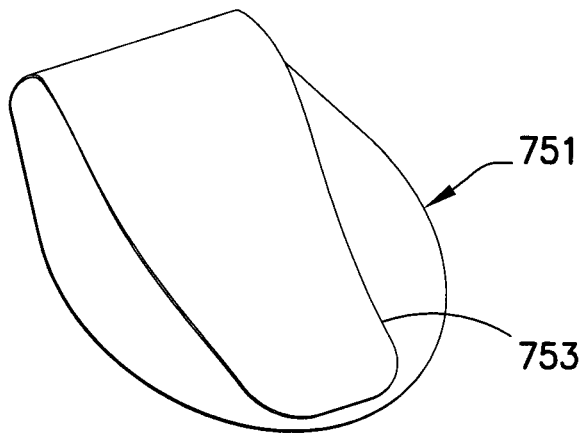
FIG. 25 is a perspective view of a label sterility barrier.

A label tab, such as label 175 of FIG. 10 or label 751 of FIG. 25, can be attached to the non-patient end of each pen needle hub and a tortuous path cap can be disposed on the patient end of the needle. The label 751 can have a handle 753 to facilitate removing the label from the pen needle hub.

A single label tab can be disposed around the entire disc storage assembly with a tortuous path between pen needles. The label tab is removed to access the first cavity, thereby removing the sterility barrier for the first pen needle. For the remaining pen needles in the disc storage assembly, the sterility barrier is provided by the tortuous path. Rotating the upper housing to the next cavity breaks the tortuous path sterility barrier for that cavity. No further removal of label tabs by the user is required.

Figure 12:
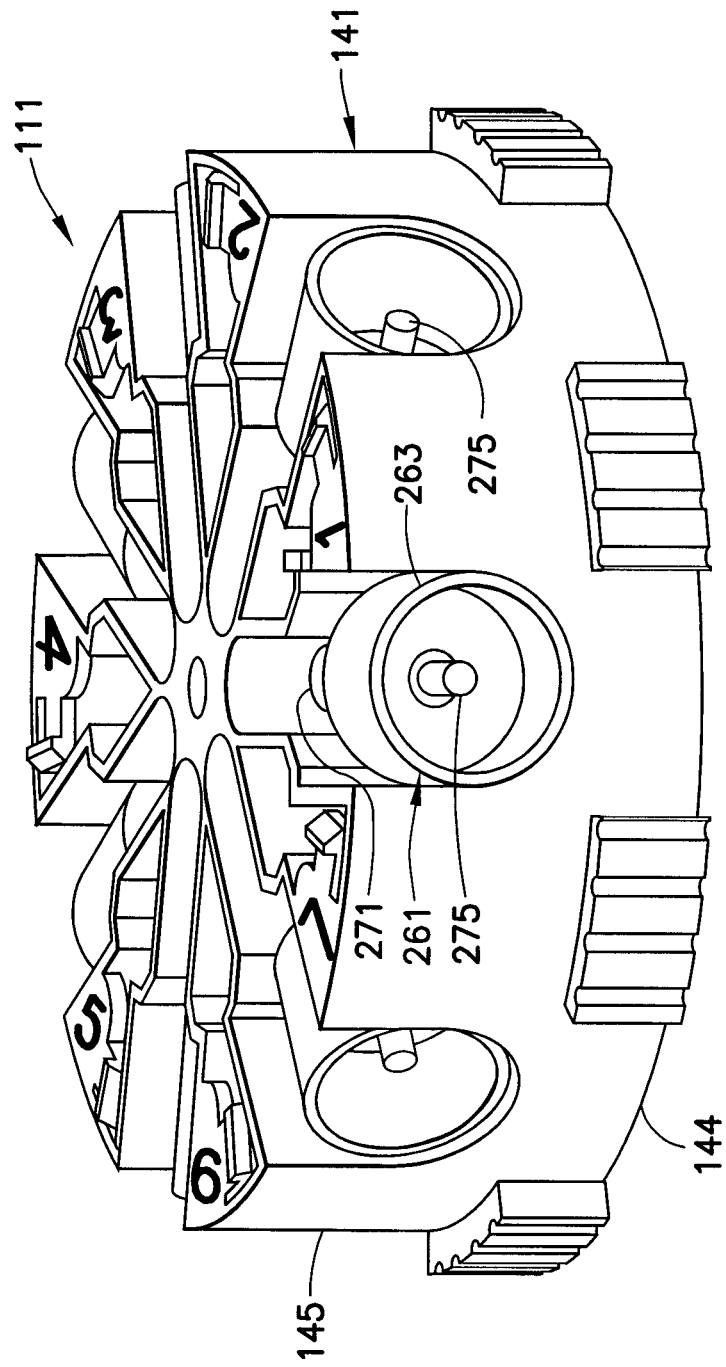
FIG. 12 is a perspective view of a lower housing of with a pen needles stored therein according to another exemplary embodiment of the present invention.

A rubber sleeve 275 can be provided on the non-patient end 166 (FIG. 11) of the pen needle 161, as shown in FIG. 12, and a shield 271 can be disposed on the patient end of the hub needle to provide sterility. The rubber sleeve 275 is compressed by the drug delivery pen when the pen is being connected to the pen needle, thereby revealing the non-patient end of the hub needle. The rubber sleeve 275 uncompresses when the used pen needle is returned to the disc storage assembly 211. Alternatively, the rubber sleeve 275 can remain uncompressed as the wall 125 of the upper housing will shield the user pen needle when the upper housing is rotated to the next position.

A sterility cap can be disposed on the patient end of the needle hub to provide sterility at the patient end of the hub needle. The sterility cap can be a shield 171 as shown in FIGS. 10 and 11 or a tortuous path sterility cap. A tortuous path sterility cap may have a tortuous path formed by a spiral thread pathway or a series of adjacent rings in which each ring has a gap disposed 180 degrees from the gap in each adjacent ring. Any suitable means may be used to form the tortuous path. A tortuous path sterility cap may be disposed on the non-patient end of the needle and the cap seals against an inner surface of the hub. The tortuous path sterility cap is manually removed by the user after connecting the needle hub to the drug delivery pen and withdrawing the pen needle from the storage assembly. Alternatively, the tortuous path sterility cap remains in the storage assembly when a pen needle is connected to a pen and the pen needle is withdrawn.

A tortuous path closure can be defined as a bather to airborne microorganisms, accomplished by creating a convoluted pathway to the product (for example, a labyrinth path or a screw-threaded closure). A tortuous path is neither airtight nor watertight. It provides a bather to ingress by microorganisms but not by fluids. Louis Pasteur, in 1861, discovered the principle of tortuous path closures. He determined that a sterilized glass flask with a swan-shaped tortuous neck, even with the end open, would remain sterile.

When microorganisms are out of liquid, they cannot move on their own and cannot turn corners. Rather, most microbes float in the air, often on dust particles. These dust-riding microbes have mass and momentum and settle by gravity. They also have static charges and are attracted to surfaces by intramolecular and electrostatic forces. Another mechanism of particle movement is Brownian motion. This random motion of particles in static airflow also causes microorganisms to impact surfaces.

With a tortuous path or labyrinth enclosure, air pressure changes cause air to move in and out of the enclosed volume. While the air moves around the turns, the organisms impact surfaces, causing them to be "filtered" out of the air. With the low air velocities caused by normal environmental pressure changes, the bacteria tend to stay where they have landed. The sterility barriers of these tortuous path closure systems are created by the repeated turns microorganisms would have to make to breach product sterility. The small air volume in many tortuous path products also helps by reducing the air volume that is exchanged with the atmosphere.

Figure 13:
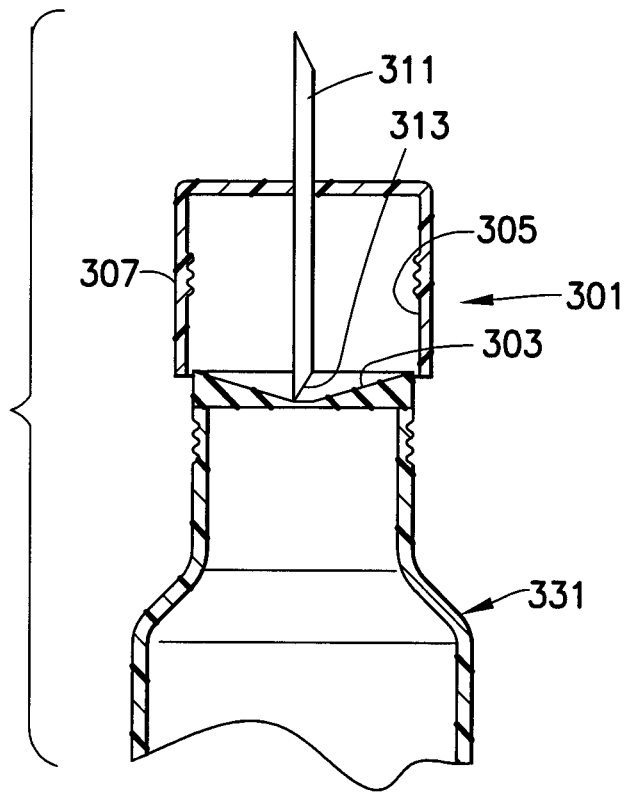
FIG. 13 is an elevational view of a pen needle having a seal member according to another exemplary embodiment of the present invention.
Figure 14:
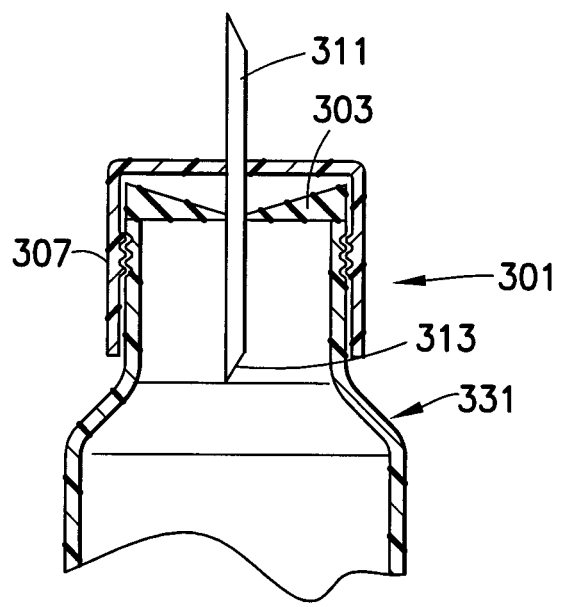
FIG. 14 is an elevational view of the pen needle of FIG. 13 with the seal member being broken after connecting the pen needle to a pen.

As shown in FIGS. 13 and 14, a pen needle 301 has a disk-shaped plug 303 that seals against the inner surface 305 of a needle hub 307 proximal to the non-patient end 313 of the needle 311. The plug 303 seals the non-patient end 313 of the needle 311 from any interaction with foreign material, thereby providing a sterility barrier. When the pen needle 301 is connected to a pen 331, the pen pushes the plug 303 through the hub 307 to a position shown in FIG. 14. The force of the pen 331 pushing the plug 303 causes the non-patient end 313 of the needle 311 to pierce the plug 303 and allow the plug to move through the hub 307. The non-patient end 313 of the needle 311 then pierces the septum 16 (FIG. 2) disposed in the pen 331.

The plug 303 can be made of either a hard or soft material, or a combination thereof. In one configuration, the material in the center of the plug 303 is softer and the material at the outer edge is harder, thereby facilitating the needle piercing the plug. Alternatively, the center of the plug 303 is thinner than the outer edge to facilitate the needle piercing the plug.

Figure 15:
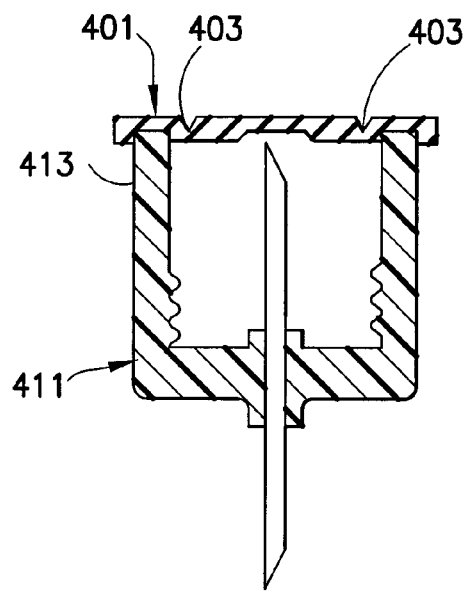
FIG. 15 is an elevational view in cross section of a barrier for a pen needle according to another exemplary embodiment of the present invention.
Figure 16:
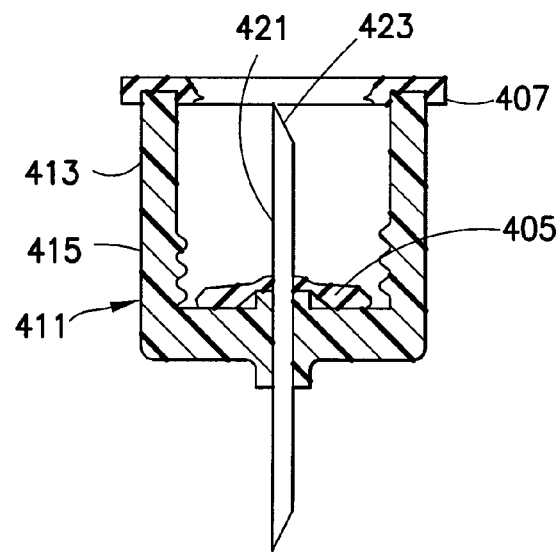
FIG. 16 is an elevational view in cross section of the pen needle of FIG. 15 after having been used with a pen to break the barrier.

As shown in FIGS. 15 and 16, a barrier 401 seals a non-patient end 413 of a pen needle 411. Preferably, the barrier 401 is made of a soft material. The barrier 401 covers the non-patient end 423 of the needle 421, thereby providing a sterility barrier. The barrier 401 has a portion 403 proximal the non-patient end 413 of the hub 415 that is thinner to facilitate being torn when the pen needle 411 is connected to a pen. Additionally, the center of the barrier 401 can be thinner to facilitate piercing the barrier with the non-patient end 423 of the needle 421. When the pen needle 411 is connected to a pen, the thinner portion 403 tears, thereby forming an inner portion 405 that moves through the hub 415 with the pen needle and an outer portion 407 that remains connected to the non-patient end 413 of the hub 415. Alternatively, the barrier 401 can have a score line or other suitable means to facilitate separating the bather into inner and outer portions when connected to a pen, as shown in FIG. 16.

Figure 17:
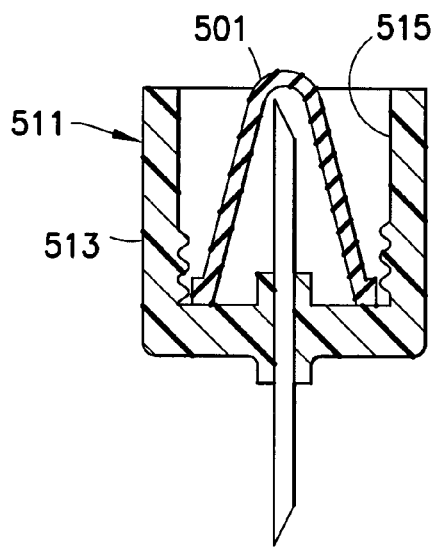
FIG. 17 is an elevational view in cross section of a pen needle having a collapsible cone according to another exemplary embodiment of the present invention.
Figure 18:
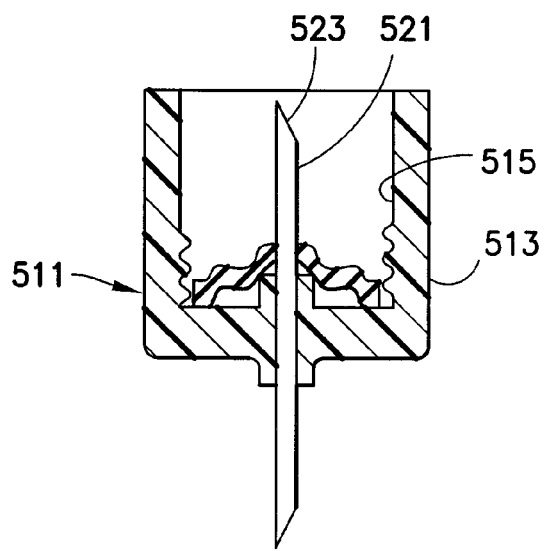
FIG. 18 is an elevational view in cross section of the pen needle of FIG. 17 after having been used with a pen to collapse the cone.
Figure 19:
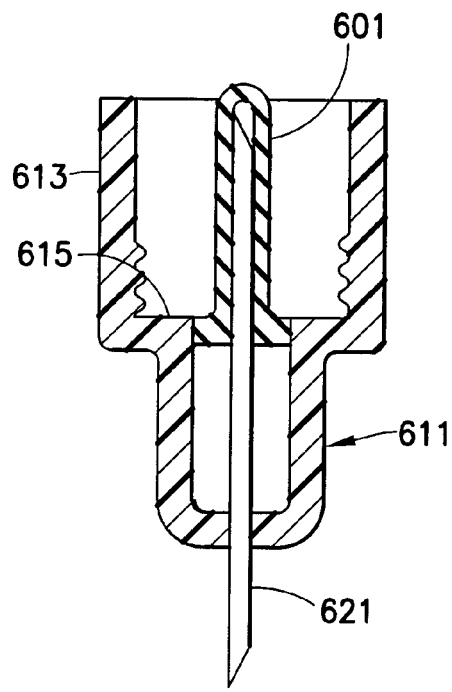
FIG. 19 is an elevational view in cross section of a pen needle having a sliding boot member according to another exemplary embodiment of the present invention.
Figure 20:
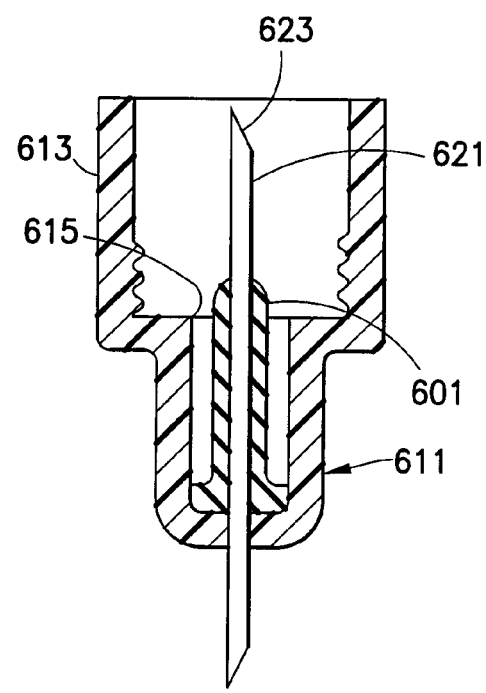
FIG. 20 is an elevational view in cross section of the pen needle of FIG. 19 after having been used with a pen to move the boot member.

As shown in FIGS. 17 and 18, a collapsible cone 501 is connected to an inner surface 515 of a hub 513 of a pen needle 511. The cone 501 covers the non-patient end 523 of the needle 521, thereby providing a sterility barrier. When the hub 513 is connected to a pen, the cone 501 is compressed, as shown in FIG. 18, thereby providing access to the non-patient end 523 of the needle 521. The cone 501 can be made of any suitable material that is pierceable by the non-patient end 523 of the needle, such as, but not limited to, rubber, plastic, paper and foil As shown in FIGS. 19 and 20, a sliding boot member 601 is connected to an inner surface 615 of a hub 613 of a pen needle 611. The boot member 601 covers the non-patient end 623 of the needle 621, thereby providing a sterility barrier. The connection between the boot member 601 and the inner surface 615 of the hub 613 creates a seal that substantially prevents microbial interaction. When the hub 613 is connected to a pen, the boot member 601 is caused to slide down the needle 621 through the hub 613. The boot member 601 can be made of any suitable material pierceable by the non-patient end 623 of the needle 621 when the hub 613 is connected to the pen. As shown in FIG. 19, the boot member 601 covers a portion of the needle 621 disposed within the hub 613, which includes the non-patient end 623 of the needle. The boot member 601 can be configured to cover any amount of the needle 621 disposed within the hub 613.

Figure 21:
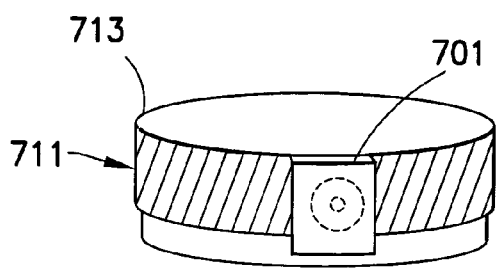
FIG. 21 is a perspective view of a disc storage assembly having a door covering a cavity.
Figure 22:
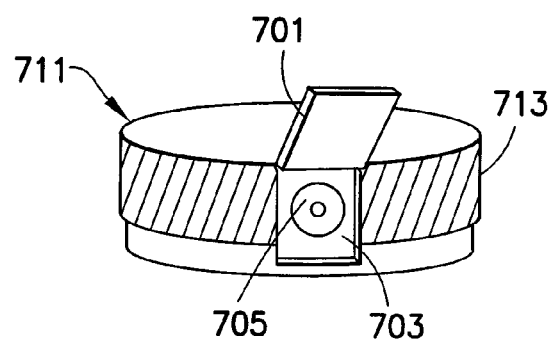
FIG. 22 is a perspective view of the disc storage assembly of FIG. 21 in which the door is open to provide access to a cavity.
Figure 23:
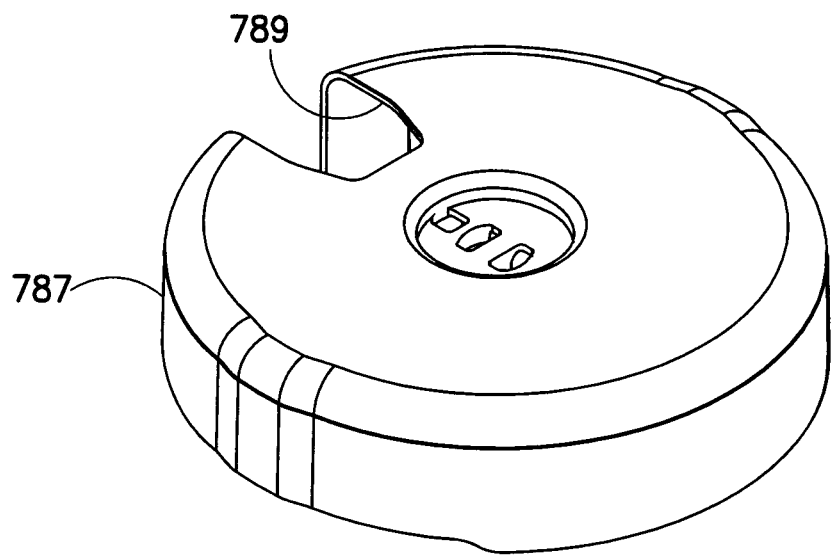
FIG. 23 is a perspective view of an upper housing of a disc storage assembly in accordance with another exemplary embodiment of the present invention.
Figure 24:
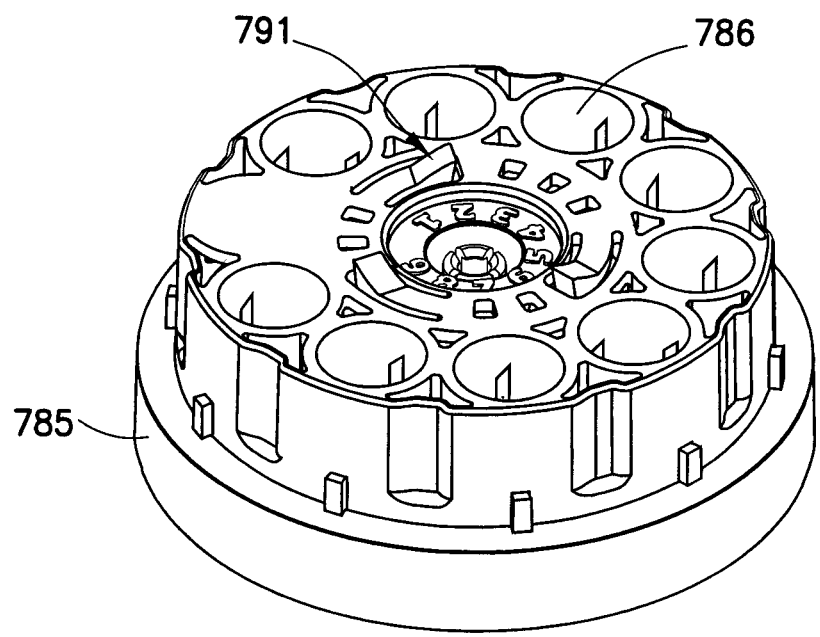
FIG. 24 is a perspective view of a lower housing of a disc storage assembly in accordance with another exemplary embodiment of the present invention.

A movable door 701 can be disposed at the access 703 to each cavity to enclose the pen needle 705 within the cavity 703, as shown in FIGS. 21 and 22. Thus, the number of doors is equal to the number of cavities in the storage assembly. The door 701 is opened to provide access to the pen needle 705 in the cavity 703, and the door 701 is closed after returning a used pen needle to the cavity 703. Accordingly, with movable doors providing access to the cavities 703, the upper housing 713 of the storage assembly 711 does not need to be rotated between cavities. The door 701 can be connected to the upper housing 713 by any suitable member, such as a living hinge. The door 701 prevents liquid or other foreign material from entering the cavity 703. Alternatively, the door 701 is connected to the upper housing 713, such that only one door connected to the upper housing is required. The door 701 can be combined with one of the other disclosed sterility barriers to further facilitate foreign material from entering the storage assembly.

A sealing member can be used to seal any access path of a cavity of the storage assembly, thereby sealing the cavity from outside fluid and weatherproofing the storage assembly. The sealing member can be a gasket, O-ring, or other suitable sealing member. The sealing member can seal the space between adjacent cavities of the storage assembly. The sealing member can also seal the upper and lower housings of the storage assembly, thereby providing sterility.

Each cavity of the storage assembly can have a pod in which the pen needle is stored. When the upper housing of the storage assembly is rotated to access a cavity, the pod opens. The upper housing of the storage assembly keeps the pod closed, until the opening (127 of FIG. 5) is rotated to that pod thereby allowing the pod to open. A pod-engaging member on the upper housing engages the pod when the upper housing is rotated to access the pod. When the used pen needle is returned to the cavity, the rotation of the upper housing causes the pod to return to the closed position.

Figure 38:
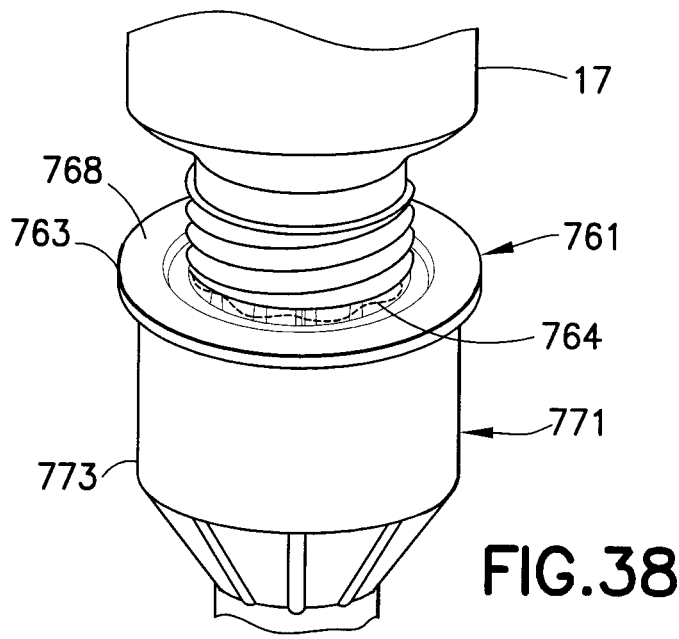
FIG. 38 is a perspective view of a drug delivery device prior to puncturing the sterility barrier of the pen needle of FIG. 36.
Figure 39:
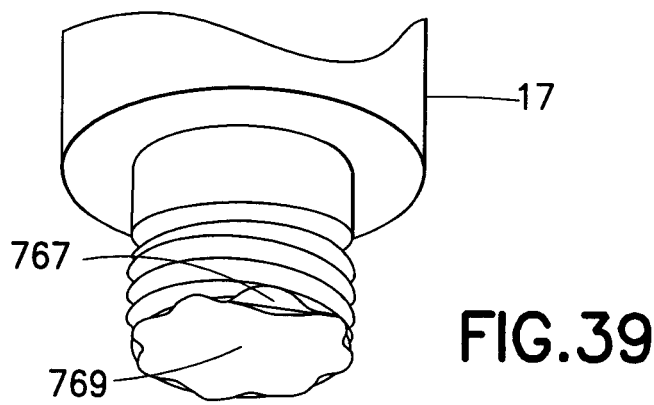
FIG. 39 is a perspective view of the drug delivery device after separating the puncturable portion of the sterility barrier.
Figure 40:
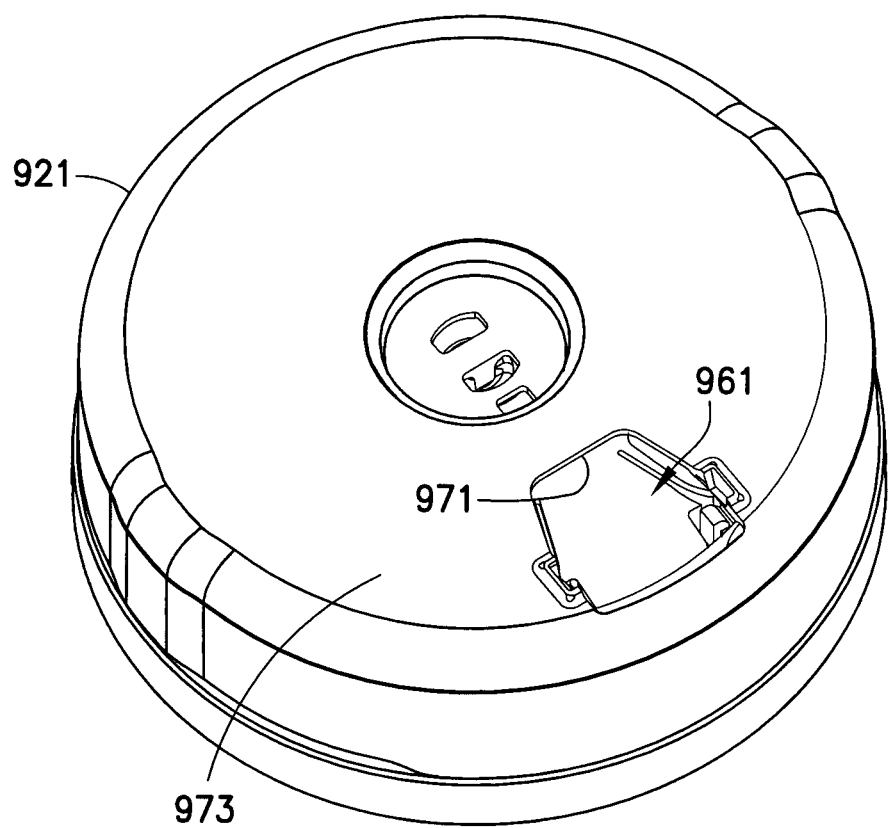
FIG. 40 is an upper perspective view of a storage assembly in an unlocked position in accordance with another exemplary embodiment of the present invention.
Figure 41:
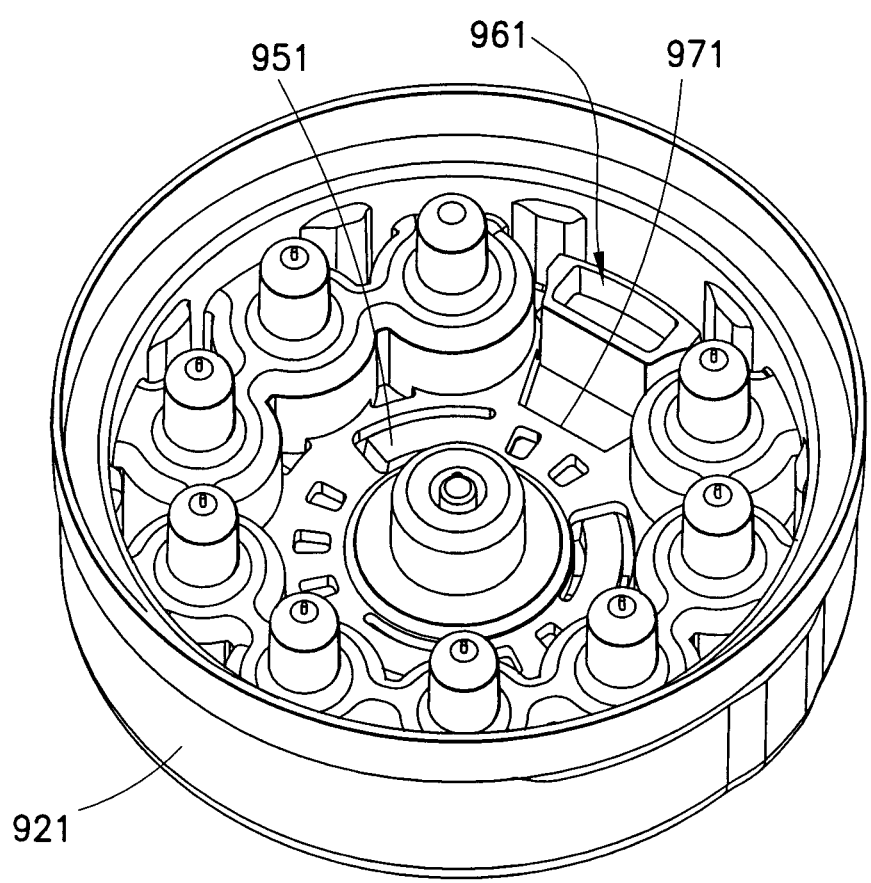
FIG. 41 is a lower perspective view of the storage assembly of FIG. 40 in an unlocked position.

An alternative sterility barrier is shown in FIGS. 26-28 and 32-39. The sterility barrier 761 is puncturable or penetrable by the lower housing 17 of the drug delivery device (FIG. 2) to access the needle of the pen needle, as shown in FIGS. 38 and 39.

Figure 1:
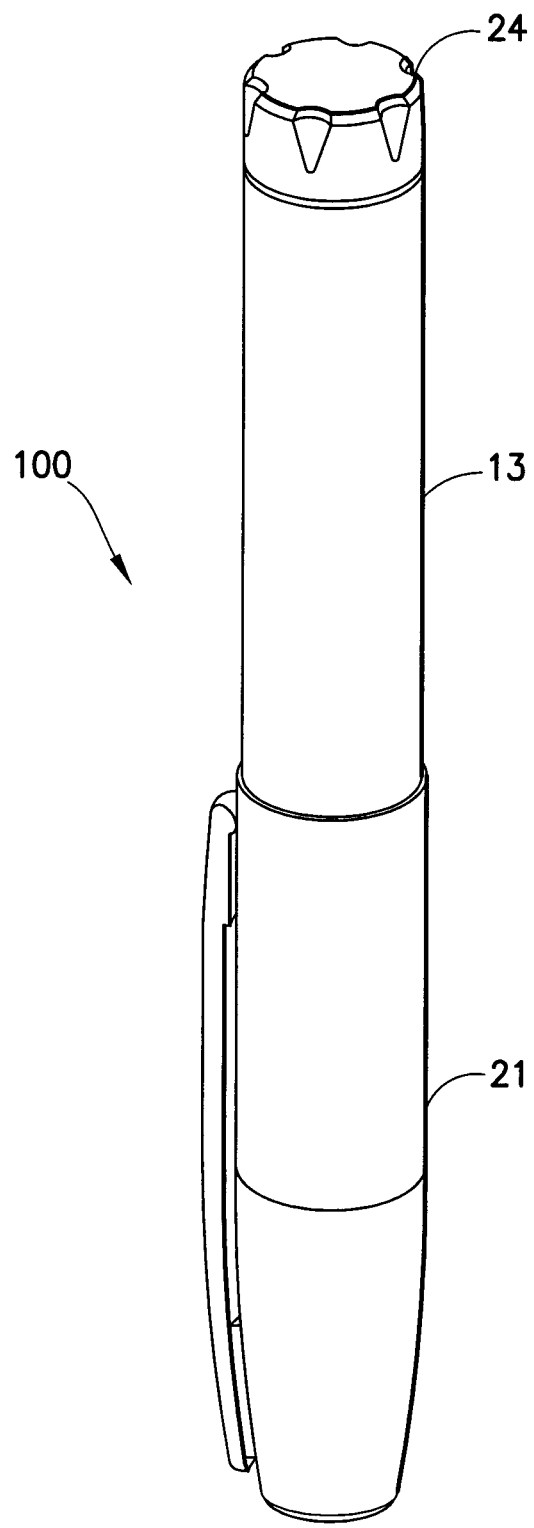
FIG. 1 is a perspective view of an assembled existing drug delivery pen.
Figure 35:
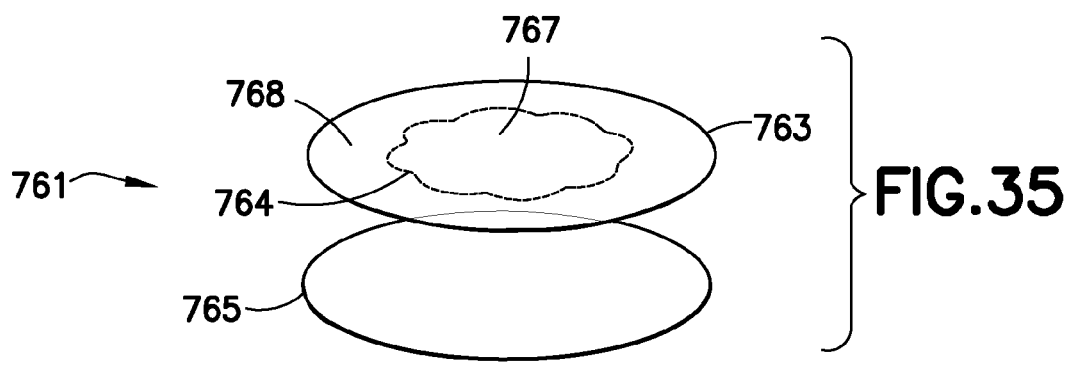
FIG. 35 is an exploded perspective view of a puncturable sterility barrier.
Figure 36:
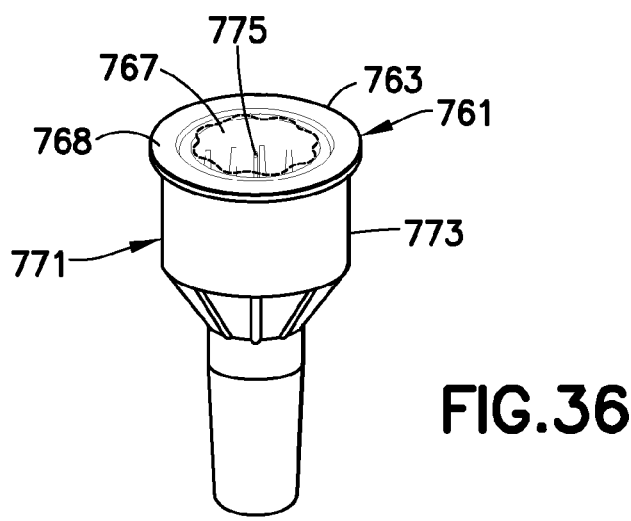
FIG. 36 is a perspective view of the puncturable sterility barrier of FIG. 35 connected to a hub of a pen needle.
Figure 37:
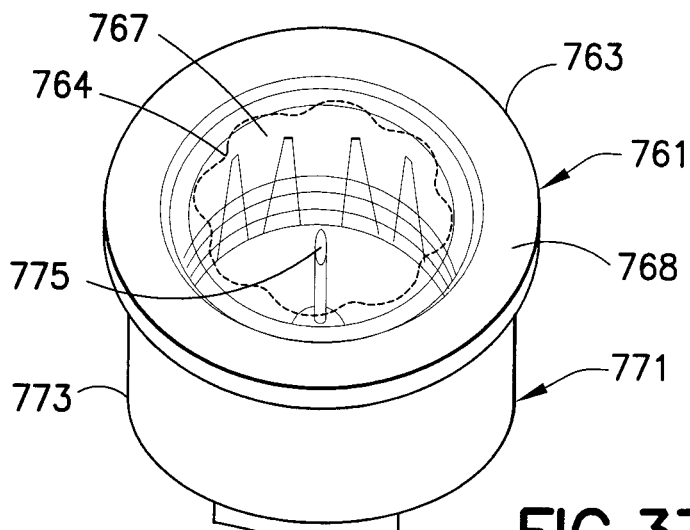
FIG. 37 is an enlarged perspective view of the pen needle having the sterility barrier of FIG. 36.

As shown in FIG. 35, the puncturable sterility barrier 761 has an upper layer 763 and a lower layer 765. Preferably, both layers 761 and 763 are thin. The upper layer has perforations 764 forming a pattern that is slightly smaller than the diameter of the lower housing 17 of the drug delivery device 100 (FIG. 1). The lower layer 765 is connected to the upper layer 763 and is preferably not perforated. The lower layer 765 provides the sterility barrier for the pen needle 771. The lower layer 765 can be a second film having similar or different properties than the upper layer 763. The lower layer 765 can also be a coating that is sprayed or sputtered onto the upper layer 763. An adhesive is bound to the sterility barrier and adheres to the hub 773 of the pen needle 771. Alternatively, the adhesive can be the lower layer and seals the perforations in the upper layer, thereby using less material for the sterility barrier 761. Alternatively, the lower layer 765 can be connected to the hub 773 of the pen needle 771 in any suitable manner, such as by heat sealing.

To access the needle 775 in the pen needle 771, the drug delivery device 100 (FIG. 1) is pushed through the sterility bather 761 connected to the pen needle 771, as shown in FIGS. 38 and 39. The perforations 764 allow a perforated portion 767 to separate from the outer portion 768 of the upper layer 763. A portion 769 of the lower layer 765 is moved with the punctured portion 767 of the upper layer 763, as shown in FIG. 39. The moved portion 767 and 769 of the sterility barrier 761 is pushed down into the hub 773 of the pen needle 771 by the lower housing 17 of the drug delivery device 100, where it remains during and following the injection. When the used pen needle 771 is returned to disc storage container or otherwise removed from the drug delivery device 100, the moved portion 767 and 769 of the sterility barrier 761 remains in the pen needle hub 773. Accordingly, a user does not need to manually peel or otherwise remove the sterility barrier 761 from the pen needle 771 or the storage container prior to connecting the pen needle to the drug delivery device.

Alternatively, a sterility barrier can be made in which both the upper and lower layers are perforated. A two-laser system can be used on a two-material substrate. An upper laser is mounted opposite a lower laser on an assembly line. The upper laser perforates only the upper material, and the lower laser perforates only the lower material. The perforation patterns are made such that they do not cross one another, but are closely nested such as, but not limited to, two concentric circular perforation patterns. By simultaneously laser perforating the upper and lower materials, there is no need to reregister the materials following the laser perforation. By eliminating the need for reregistration, concentricity tolerances are eliminated from registration and tighter tolerance perforation patterns can be made. This allows the perforation patterns to be closer together on top of one another, thereby providing a more predictable separating performance.

Alternatively, a puncturable sterility barrier can be made of a single layer. The layer is perforated such that the perforations do not extend entirely through the thickness of the layer. The perforation depth is less than the thickness of the layer, such that the layer is partially perforated. Accordingly, the partially perforated layer maintains sterility prior to use because there is no perforation or opening extending completely through the layer through microbes can enter. When force is applied to the partially perforated layer by the lower housing of the drug delivery device, the partial perforations allow the perforated portion to separate and expose the needle of the pen needle. By forming the sterility barrier with a single partially perforated layer, the manufacturing complexities of converting and laminating two or more layers is avoided.

Figure 26:
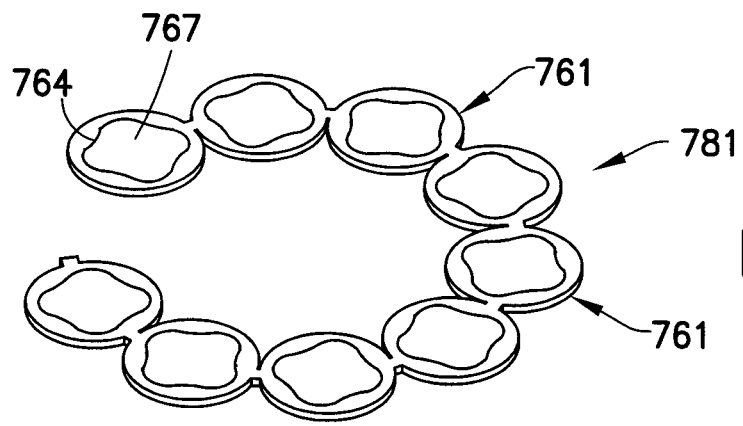
FIG. 26 is a perspective view of a puncturable sterility barrier.
Figure 27:
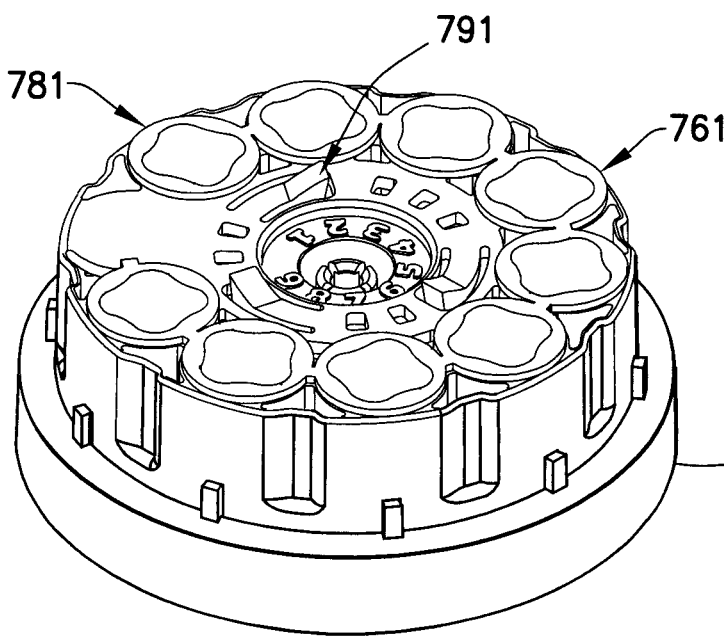
FIG. 27 is a perspective view of the lower housing of FIG. 24 to which the puncturable sterility barrier of FIG. 26 is connected.
Figure 28:
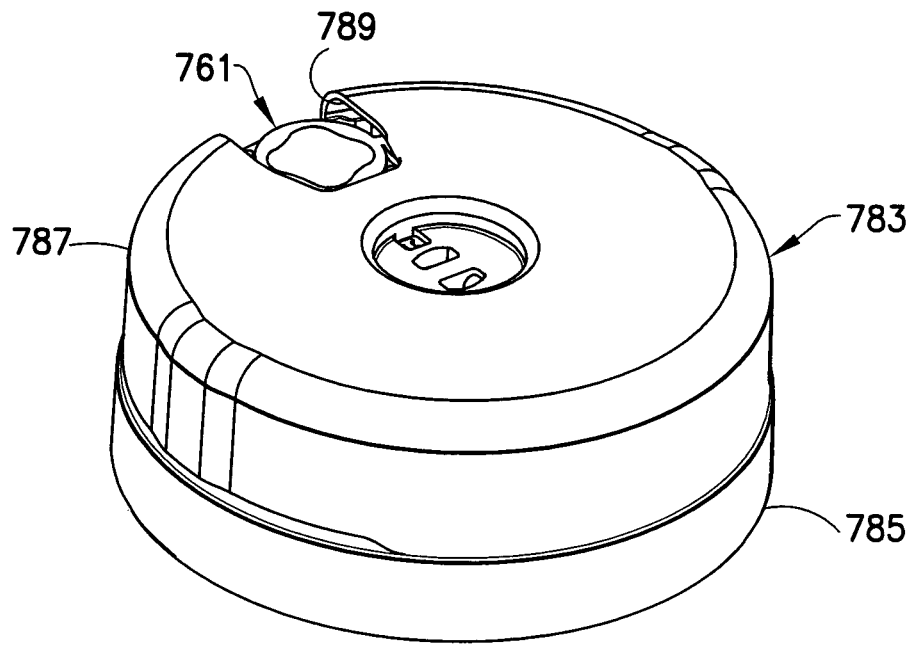
FIG. 28 is a perspective view of an assembled disc storage assembly having the puncturable sterility barrier of FIG. 26.

As shown in FIGS. 26 and 27, a plurality of puncturable sterility barriers 761 are connected together to form a chain 781 of sterility barriers for use with a top access storage container 783. As shown in FIG. 27, each sterility barrier 761 of the chain 781 is connected to a pen needle, such as with adhesive or in any other suitable manner.

Figure 29:
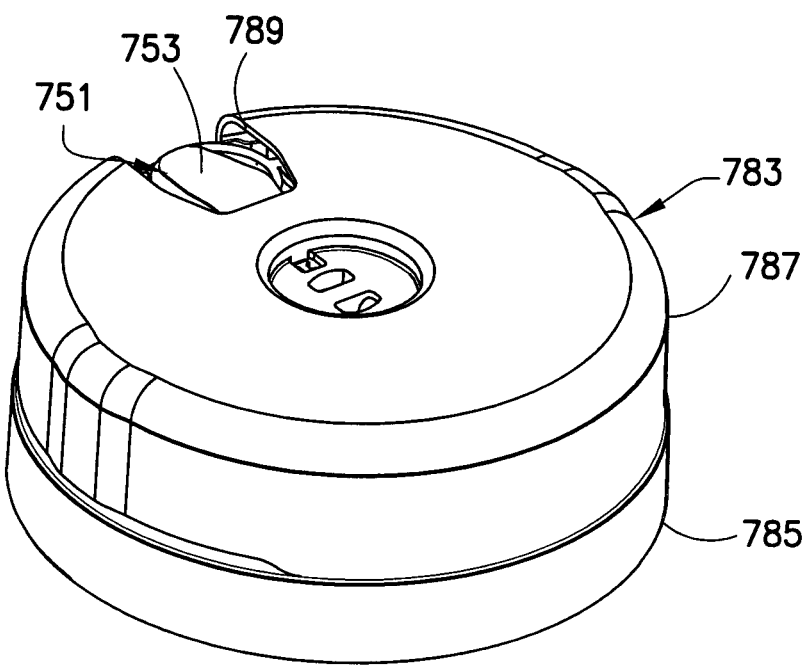
FIG. 29 is a perspective view of an assembled disc storage assembly having the label sterility barrier of FIG. 25.
Figure 30:
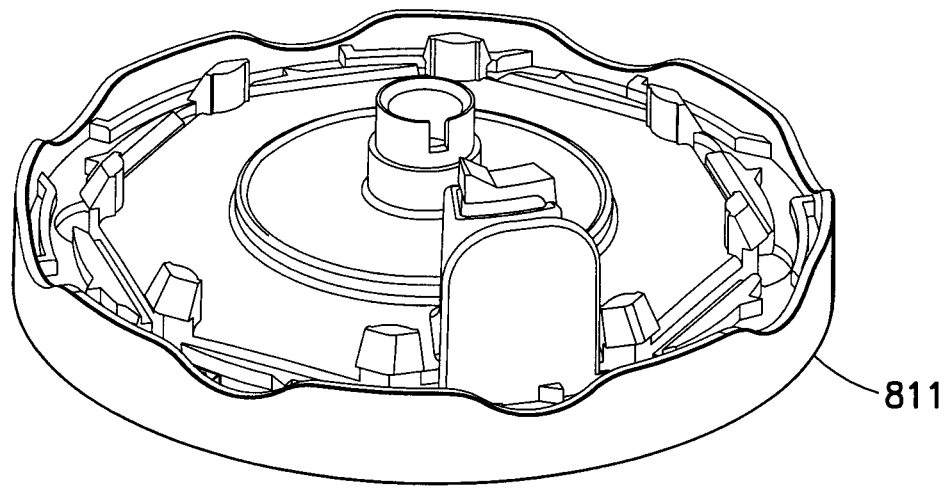
FIG. 30 is a perspective view of a lower housing of a disc storage assembly in accordance with another exemplary embodiment of the present invention.
Figure 31:
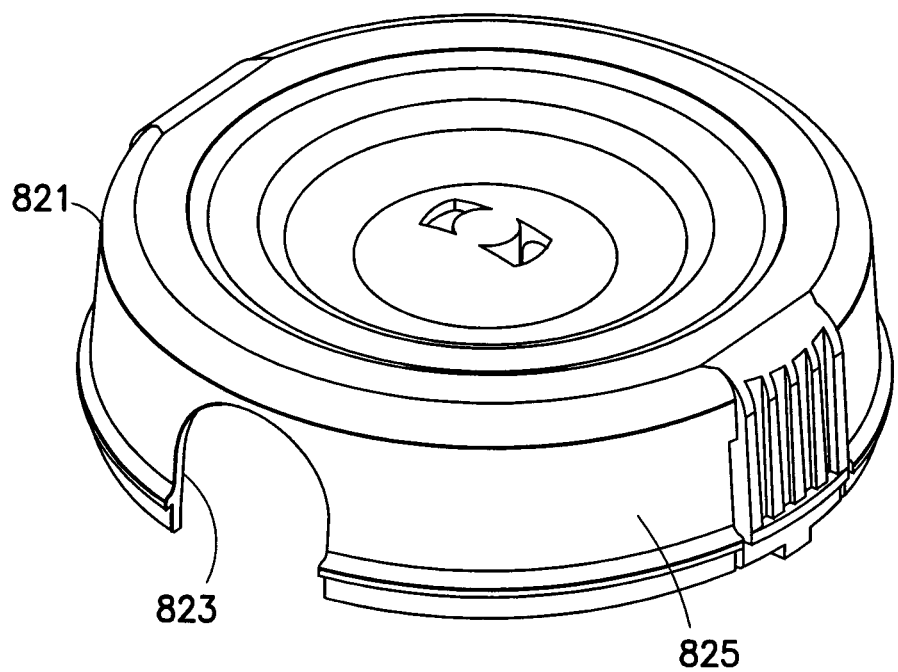
FIG. 31 is a perspective view of an upper housing of a disc storage assembly in accordance with another exemplary embodiment of the present invention.
Figure 32:
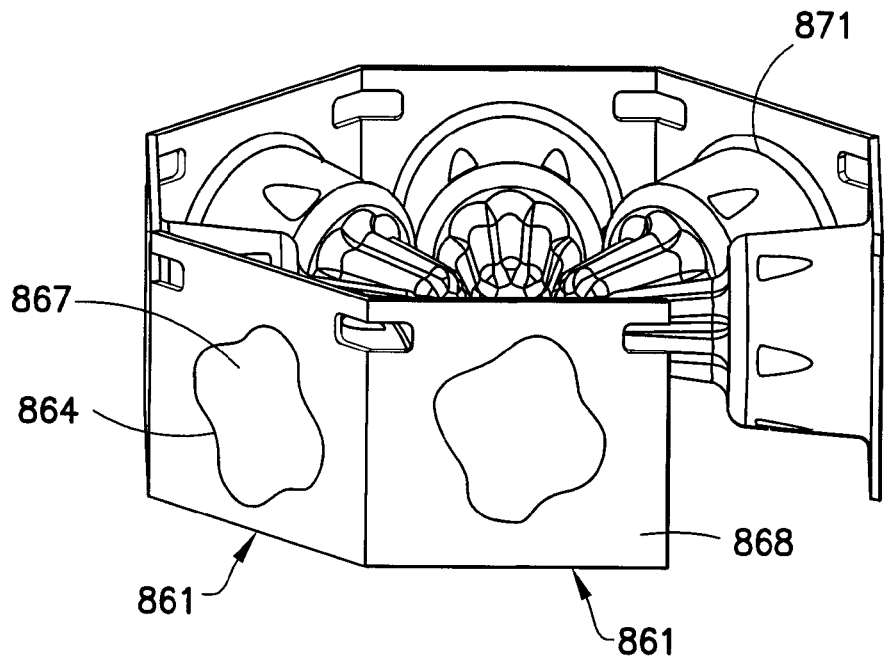
FIG. 32 is a perspective view of a sterility barrier assembly having a plurality of puncturable sterility barriers to which pen needles are connected.
Figure 33:
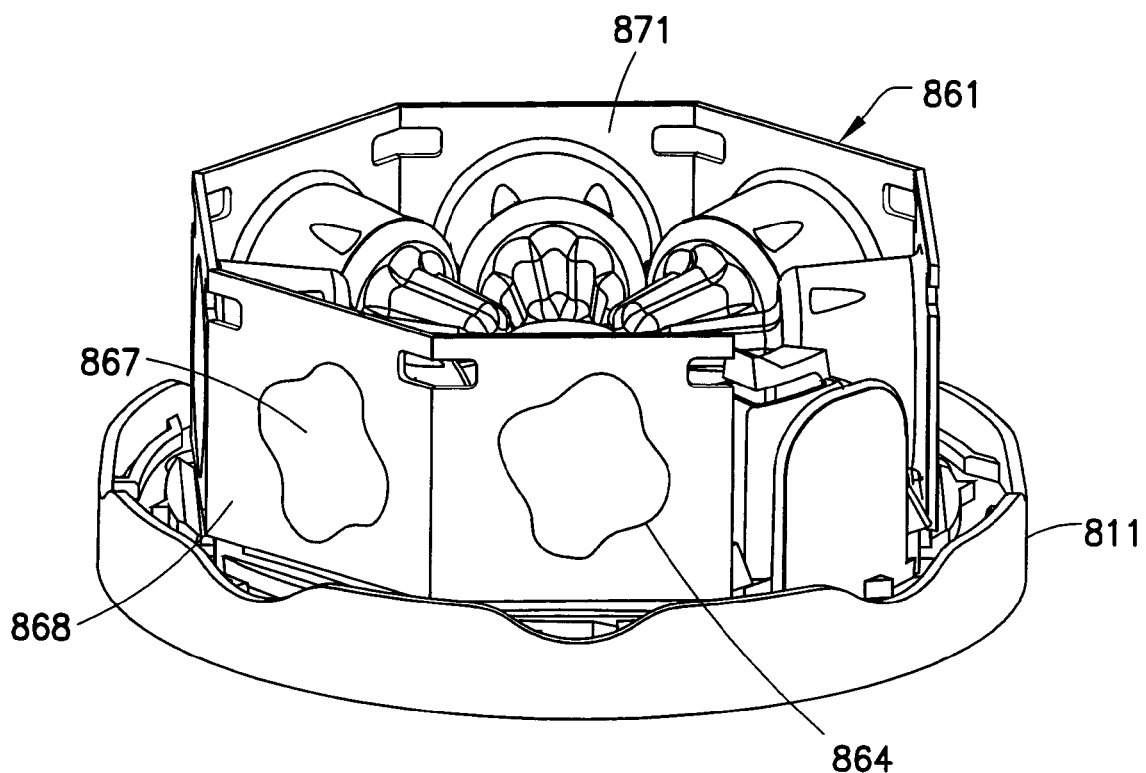
FIG. 33 is a perspective view of the sterility barrier assembly of FIG. 32 disposed in the lower housing of FIG. 30.
Figure 34:
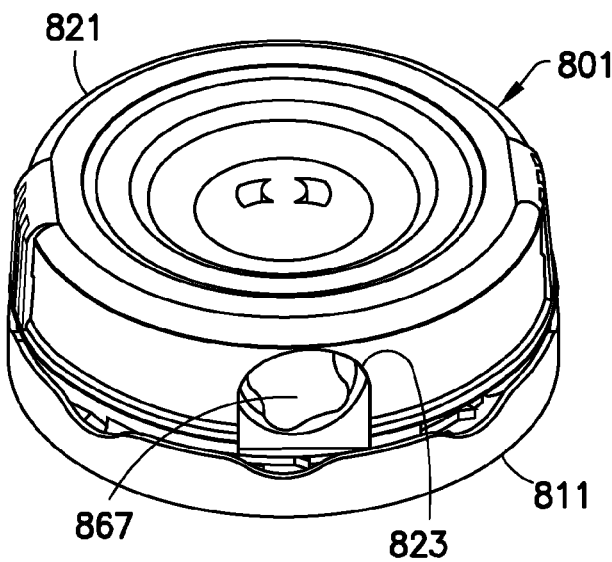
FIG. 34 is a perspective view of an assembled disc storage assembly having the sterility barrier assembly of FIG. 32.

The pen needles with attached puncturable sterility barriers 761 are disposed in cavities 786 in a lower housing 785 of a top access storage assembly 783, as shown in FIGS. 23, 24, and 27-29. Accordingly, the sterility bathers 761 face upwardly. The upper housing 787 is then rotatably connected to the lower housing 785. Access to the pen needles stored in the cavities 786 in the lower housing 785 is provided through a recess 789 in the upper housing 787. The top access storage assembly 783 operates substantially similarly to the side access storage assembly 111 of FIG. 3. As shown in FIG. 29, a top access storage assembly 783 receives a plurality of pen needles using peelable labels 751 of FIG. 25 as the sterility barrier for the pen needle.

As shown in FIGS. 30-34, a top access storage assembly 801 accommodates a plurality of puncturable sterility barriers 861. The puncturable sterility barrier 861 is substantially similar to the puncturable sterility barrier of FIGS. 35-39. Perforations 864 define a perforated, or movable, portion 867 of the sterility barrier 861. The outer portion 868 of the sterility barrier 861 remains in the lower housing 811 of the storage assembly 801. The plurality of sterility barriers 861 are connected on both sides to adjacent sterility barriers except for the first and last sterility barriers, which have only one sterility barrier connected thereto. A pen needle 871 is connected to each puncturable sterility barrier 861, such as with an adhesive.

The plurality of sterility barriers 861 and pen needles 871 are disposed in the base of the side access storage assembly 801. An upper housing 821 having a recess 823 in a side wall 825 is rotatably connected to the lower housing 811 to form the side access storage assembly 801. The side access storage assembly is substantially similar to the side access storage assembly 111 of FIG. 3.

Another exemplary embodiment of a side access storage assembly 901 is shown in FIGS. 40-45. The side access storage assembly 901 is substantially similar to the storage assembly 111 of FIG. 3. An upper housing 921 is rotatably connected to a lower housing 911. A recess 923 in a side wall 925 of the upper housing 921 provides access to the pen needles stored in the lower housing.

Figure 44:
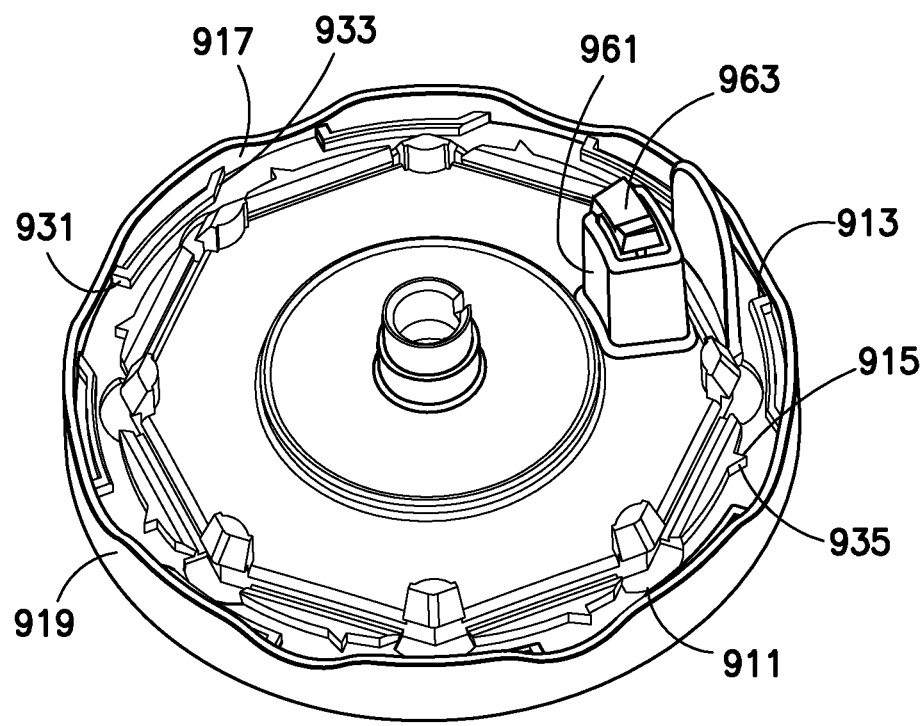
FIG. 44 is a perspective view of a lower housing of a storage assembly in accordance with another exemplary embodiment of the present invention.

Protrusions 927 are oppositely disposed on the upper housing 921, as shown in FIG. 45. The protrusions 927 extend from flexible buttons 929. A first plurality of stop members 913 are formed on an inner surface 917 of the base wall 919, as shown in FIG. 44. The first plurality of stop members 913 extend between the pen needles disposed in the lower housing 911. The first stop members 913 have a first end 931 proximate a pen needle and a second end 933 proximate the adjacent pen needle. A second plurality of stop members 915 are disposed radially inwardly of the first plurality of stop members 913. The second plurality of stop members 915 are disposed at the pen needle access area.

The protrusions 927 on the upper housing 921 engage the first ends 931 of the first stops 913, thereby preventing rotation of the upper housing. The recess 923 in the upper housing 921 is disposed in a position to access a pen needle. When an injection has been made, the used pen needle is returned to the storage assembly 901. When the user is ready to make another injection, the flexible buttons 929 are pushed inwardly, thereby moving the protrusions 927 inwardly and out of engagement with the first stop member 913. The upper housing 921 is rotated until the protrusions 927 engage a ramped surface 935 on the adjacent second stop member 915. This moves the protrusions 927 radially outwardly and into engagement the first end 931 of the next first stop member 913. The recess 923 in the upper housing 921 is now in position to access the next pen needle. Accordingly, the first and second stop members and the protrusions 927 guide rotation of the upper housing between pen needles, thereby preventing over-rotation.

A plurality of tabs 941 are disposed on an inner surface 943 of the upper housing 921, as shown in FIG. 45. Each tab 941 has a ramped surface 945 and a stop surface 949. The stop surface 949 extends substantially perpendicularly to the inner surface 943 from which the tab 941 extends. The tabs 941 engage the flexible fingers 951 (or fingers 191 of FIG. 6 or fingers 791 of FIGS. 24 and 27) in the lower housing 911. The ramped surfaces 947 of the tabs 941 engage corresponding ramped surfaces of the fingers 951, thereby deflecting the fingers 951 downwardly and allowing the upper housing to rotate. When the upper housing 921 is rotated in the opposite direction, such as to access a used pen needle, the stop surfaces 949 of the tabs 941 engage corresponding surfaces on the fingers 951, thereby preventing rotation of the upper housing 921 in that direction such that used pen needles cannot be accessed.

Figure 42:
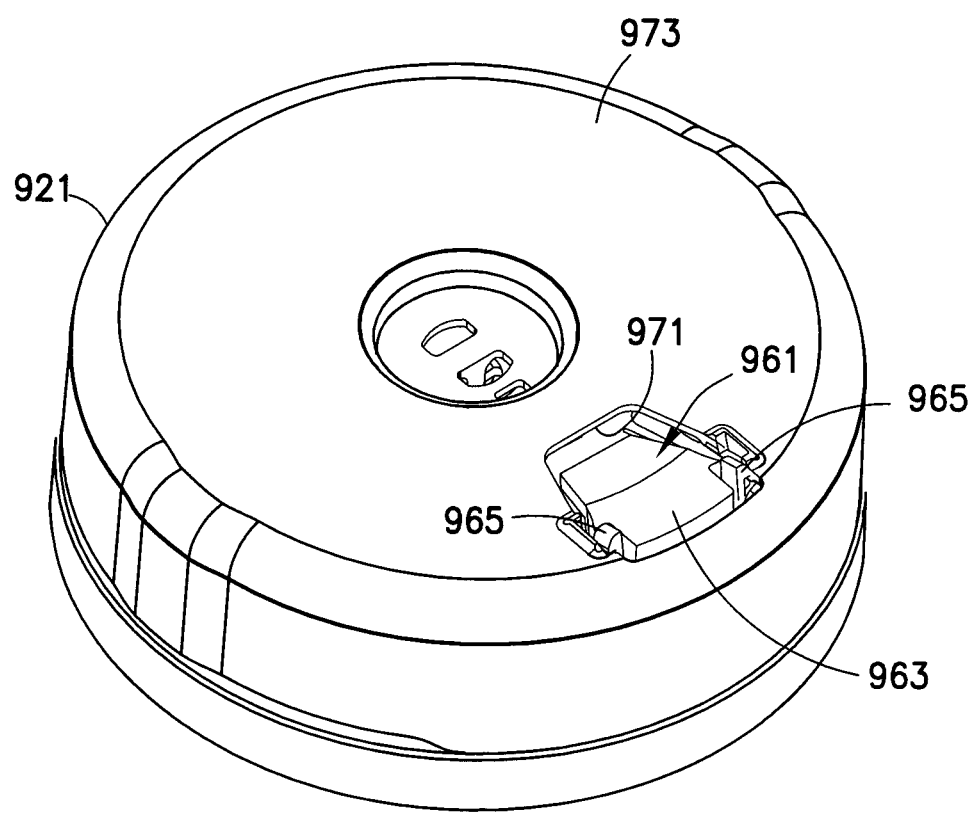
FIG. 42 is a upper perspective view of the storage assembly of FIG. 40 in a locked position.

A locking member 961 is connected to the lower housing 911. The locking member includes a post 963 and locking tabs 965. The post 963 is accessible from a lower surface of the lower housing 911. When the storage assembly 901 is to be locked, such as when all the pen needles have been used, the user pushes the post 963 upwardly. The post passes through the access opening 971 in an upper surface of the upper housing 921. The locking tabs 965 latch onto the upper surface 973 of the upper housing 921, thereby preventing further rotation of the upper housing 921, as shown in FIG. 42. As shown in FIG. 44, the locking member 961 is disposed in the lower housing in a position where no pen needles are stored, such that when the storage assembly 901 is locked there is no access to a pen needle. Accordingly, access to all pen needles is prevented.

Another alternative sterility barrier is a single ribbonlike member wrapped around the entire lower housing, thereby covering each cavity access. The ribbonlike member can be made of a common material, such as, but not limited to, paper, foil, plastic or rubber. A cutting tool, such as a blade, can be disposed on the upper housing such that rotation of the upper housing causes the blade to slice the ribbon, thereby allowing a drug delivery pen to pass through the ribbon to access the pen needle in the cavity. The cut is made in the ribbonlike member in front of the cavity being accessed, such that the remaining ribbonlike member is uncut and still provides a sterile barrier for the pen needles disposed in those cavities covered by the uncut ribbonlike member.

Many of the various means of providing sterility allow new pen needles to be individually sealed in cavities of the disc storage assembly. Pen needles can be manufactured using existing processes and assembled into the disc storage assembly with few or no additional steps, thereby simplifying the manufacturing process.

A manual lock can be provided on the pen needle storage assembly, thereby allowing the user to manually lock the storage assembly to allow for safe disposal thereof. Preferably, such lock becomes functional only after the last pen needle has been used.

In another exemplary embodiment of the present invention, each used pen needle remains accessible such that the user has access to the used pen needles in case of an emergency. Alternatively, only one pen needle is always accessible, thereby providing an available pen needle in case of emergency. The other pen needles are locked into the storage assembly and are no longer accessible.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

What is claimed is:

1. A pen needle, comprising:
    a hub having a first opening and a second opening;
    a needle connected to said hub and extending through said first opening and comprising a non-patient portion extending toward said second opening; and
    a sterility barrier protecting said non-patient portion of said needle, said sterility barrier having a portion that is movable on said needle along a longitudinal axis of said needle to provide access to said non-patient portion of said needle;
    wherein said sterility barrier is not removed from said-pen needle prior to use with an injection apparatus.

2. The pen needle according to claim 1, wherein said entire sterility barrier is movable to provide access to said needle.

3. The pen needle according to claim 2, wherein a center of said sterility barrier has a thinner thickness than an edge thereof.

4. The pen needle according to claim 2, wherein said sterility barrier is movable from a first position covering said needle to a second position in which said needle is uncovered by a drug delivery pen being connected to said pen needle hub.

5. The pen needle according to claim 4, wherein said sterility barrier returns to said first position when the drug delivery pen is disconnected from said pen needle hub.

6. The pen needle according to claim 1, wherein said movable portion separates from a fixed portion of said sterility barrier to provide access to said needle.

7. The pen needle according to claim 6, wherein said movable portion of said sterility barrier is defined by a perforation to facilitate separation of said movable portion from said fixed portion.

8. The pen needle according to claim 1, wherein said sterility barrier includes a perforated first layer and a second layer connected to said first layer.

9. The pen needle according to claim 8, wherein said second layer comprises an adhesive.

10. The pen needle according to claim 8, wherein one of said first and second layers comprises a paper material and said other layer comprises a plastic material.

11. A pen needle storage container, comprising:
    a plurality of pen needles, each said pen needle having a hub with first and second openings and a needle connected to said hub and passing through said first opening;
    a housing having a plurality of cavities to receive said plurality of pen needles;
    a cover rotatably connected to said housing, said cover being rotated such that an access portion in said cover is aligned with one of said cavities to provide access to said pen needle in said cavity; and
    a sterility barrier preventing access to said needle, a portion of said sterility barrier being movable on said needle to access said needle;
    wherein, when the pen needle storage container is connected to an injector pen, the needle pierces the sterility barrier to enable said portion of said sterility barrier to move on said needle; and
    wherein said sterility barrier is not removed from said pen needle prior to use with an injection apparatus.

12. The pen needle storage container according to claim 11, wherein said access portion is in an upper surface of said cover.

13. The pen needle storage container according to claim 11, wherein said access portion is in a side wall of said cover.

14. The pen needle storage container according to claim 11, wherein said sterility barrier is connected to said pen needle.

15. The pen needle storage container according to claim 11, wherein said sterility barrier is connected to said housing.

16. The pen needle storage container according to claim 11, wherein a first plurality of arms connected to said housing engage a second plurality of arms connected to said cover to allow rotation of said cover in only one direction.

17. The pen needle storage container according to claim 11, wherein said plurality of needles are received by said plurality of cavities after being used for an injection.

18. A method of connecting a pen needle to a drug delivery pen, comprising the steps of:
    moving a portion of a sterility barrier protecting a non-patient end of a needle extending into a pen needle hub along a longitudinal axis of the needle with the drug delivery pen; and
    connecting the drug delivery pen with the pen needle hub to create a fluid path between a medicament cartridge of the drug delivery pen and the needle of the pen needle after the sterility barrier is pierced by the needle;
    wherein said sterility barrier is not removed from said-pen needle prior to use with said drug delivery pen.

19. The method of connecting a pen needle to a drug delivery pen according to claim 18, wherein the step of moving the portion of the sterility barrier includes moving a perforated portion of the sterility barrier into the pen needle hub with the drug delivery pen.

20. The method of connecting a pen needle to a drug delivery pen according to claim 18, further comprising the step of:
    removing the pen needle hub from a storage container after connecting the drug delivery pen to the pen needle hub.

* * * * *